(12) United States Patent
Gertner

(10) Patent No.: US 7,822,175 B2
(45) Date of Patent: Oct. 26, 2010

(54) PORTABLE ORTHOVOLTAGE RADIOTHERAPY

(75) Inventor: Michael Gertner, Menlo Park, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 23 days.

(21) Appl. No.: 11/833,939

(22) Filed: Aug. 3, 2007

(65) Prior Publication Data

US 2008/0144771 A1 Jun. 19, 2008

Related U.S. Application Data

(60) Provisional application No. 60/933,220, filed on Jun. 4, 2007, provisional application No. 60/922,741, filed on Apr. 9, 2007, provisional application No. 60/869,872, filed on Dec. 13, 2006, provisional application No. 60/862,210, filed on Oct. 19, 2006, provisional application No. 60/862,044, filed on Oct. 18, 2006, provisional application No. 60/829,676, filed on Oct. 16, 2006.

(51) Int. Cl.
*A61N 5/10* (2006.01)
*G21K 5/08* (2006.01)
*A61B 6/00* (2006.01)

(52) U.S. Cl. .................. 378/65; 378/68; 600/429

(58) Field of Classification Search .......... 378/65, 378/68; 606/1–6, 10, 13, 17, 107, 130; 600/1, 600/2, 407, 425–429; 604/19, 20
See application file for complete search history.

(56) References Cited

U.S. PATENT DOCUMENTS

| 3,073,960 | A | 1/1963 | Guentner et al. |
| 4,521,905 | A | 6/1985 | Hosokawa |
| 4,710,193 | A | 12/1987 | Volk |
| 4,718,418 | A | 1/1988 | L'Esperance, Jr. |

(Continued)

FOREIGN PATENT DOCUMENTS

WO    WO 01/26591    4/2001

(Continued)

OTHER PUBLICATIONS

Wanbao, Gao and David Raeside, Orthovoltage Radiation Therapy Treatment Planning Using Monte Carlo Simulation: Treatment of Neuroendocrine Carcinoma of the Maxillary Sinus; Phys. Med. Biol., 1997, pp. 2421-2433, vol. 42, United Kingdom.

(Continued)

*Primary Examiner*—Edward J Glick
*Assistant Examiner*—Anastasia Midkiff
(74) *Attorney, Agent, or Firm*—McDermott Will & Emery LLP; James W. Hill; M. Todd Hales

(57) ABSTRACT

A portable orthovoltage radiotherapy system is described that is configured to deliver a therapeutic dose of radiation to a target structure in a patient. In some embodiments, inflammatory ocular disorders are treated, specifically macular degeneration. In some embodiments, the ocular structures are placed in a global coordinate system based on ocular imaging. In some embodiments, the ocular structures inside the global coordinate system lead to direction of an automated positioning system that is directed based on the ocular structures within the coordinate system.

22 Claims, 20 Drawing Sheets

U.S. PATENT DOCUMENTS

| | | | |
|---|---|---|---|
| 4,817,432 A | 4/1989 | Wallace et al. | |
| 5,008,907 A | 4/1991 | Norman et al. | |
| 5,027,818 A | 7/1991 | Bova et al. | |
| 5,139,494 A | 8/1992 | Freiberg | |
| 5,171,254 A | 12/1992 | Sher | |
| 5,189,687 A | 2/1993 | Bova et al. | |
| 5,207,223 A | 5/1993 | Adler | |
| 5,216,255 A | 6/1993 | Weidlich | |
| 5,304,167 A | 4/1994 | Freiberg | |
| 5,336,215 A | 8/1994 | Hsueh et al. | |
| 5,339,347 A | 8/1994 | Slatkin et al. | |
| 5,354,323 A | 10/1994 | Whitebook | |
| 5,373,844 A | 12/1994 | Smith et al. | |
| 5,411,026 A | 5/1995 | Carol | |
| 5,427,097 A | 6/1995 | Depp | |
| 5,430,308 A | 7/1995 | Feichtner et al. | |
| 5,468,238 A | 11/1995 | Mersch | |
| 5,528,652 A | 6/1996 | Smith et al. | |
| 5,556,417 A | 9/1996 | Sher | |
| 5,635,721 A | 6/1997 | Bardi et al. | |
| 5,644,616 A | 7/1997 | Landi et al. | |
| 5,651,043 A | 7/1997 | Tsuyuki et al. | |
| 5,668,847 A | 9/1997 | Hernandez | |
| 5,708,696 A | 1/1998 | Kantor | |
| 5,724,400 A | 3/1998 | Swerdloff et al. | |
| 5,727,042 A | 3/1998 | Brenneisen | |
| 5,737,384 A | 4/1998 | Fenn | |
| 5,744,919 A | 4/1998 | Mishin et al. | |
| 5,745,545 A | 4/1998 | Hughes | |
| 5,771,270 A | 6/1998 | Archer | |
| 5,778,043 A | 7/1998 | Cosman | |
| 5,820,553 A | 10/1998 | Hughes | |
| 5,870,697 A | 2/1999 | Chandler et al. | |
| 5,901,199 A | 5/1999 | Murphy et al. | |
| 6,001,054 A | 12/1999 | Regulla et al. | |
| 6,104,778 A | 8/2000 | Murad | |
| 6,126,668 A | 10/2000 | Bair et al. | |
| 6,134,294 A | 10/2000 | Gibbs | |
| 6,135,996 A | 10/2000 | Kolesa et al. | |
| 6,144,875 A | 11/2000 | Schweikard et al. | |
| 6,245,059 B1 | 6/2001 | Clapham | |
| 6,257,722 B1 | 7/2001 | Toh | |
| 6,260,005 B1 | 7/2001 | Yang et al. | |
| 6,278,764 B1 | 8/2001 | Barbee, Jr. et al. | |
| 6,287,299 B1 | 9/2001 | Sasnett et al. | |
| 6,299,054 B1 | 10/2001 | Gibbs, Jr. | |
| 6,299,307 B1 | 10/2001 | Oltean et al. | |
| 6,301,328 B1 | 10/2001 | Sliski et al. | |
| 6,359,963 B1 | 3/2002 | Cash | |
| 6,385,286 B1 * | 5/2002 | Fitchard et al. | 378/65 |
| 6,436,113 B1 | 8/2002 | Burba et al. | |
| 6,459,762 B1 | 10/2002 | Wong et al. | |
| 6,494,878 B1 | 12/2002 | Pawlowski et al. | |
| 6,501,981 B1 | 12/2002 | Schweikard et al. | |
| 6,512,813 B1 | 1/2003 | Krispel et al. | |
| 6,535,574 B1 | 3/2003 | Collins et al. | |
| 6,560,312 B2 | 5/2003 | Cash | |
| 6,690,965 B1 | 2/2004 | Riaziat et al. | |
| 6,714,620 B2 | 3/2004 | Caflisch et al. | |
| 6,728,335 B1 | 4/2004 | Thomson et al. | |
| 6,744,846 B2 | 6/2004 | Popescu et al. | |
| 6,778,850 B1 | 8/2004 | Adler et al. | |
| 6,789,900 B2 | 9/2004 | Van de Velde | |
| 6,792,073 B2 | 9/2004 | Deasy et al. | |
| 6,810,107 B2 | 10/2004 | Steinberg | |
| 6,837,862 B2 | 1/2005 | Driver, Jr. | |
| 6,863,667 B2 | 3/2005 | Webb et al. | |
| 6,865,253 B2 | 3/2005 | Blumhofer et al. | |
| 6,865,254 B2 | 3/2005 | Nafstadius | |
| 6,888,919 B2 | 5/2005 | Graf | |
| 6,937,696 B1 | 8/2005 | Mostafavi | |
| 6,942,656 B2 | 9/2005 | Pawlowski et al. | |
| 6,965,847 B2 | 11/2005 | Wessol et al. | |
| 6,977,987 B2 | 12/2005 | Yamashita et al. | |
| 6,990,175 B2 | 1/2006 | Nakashima et al. | |
| 7,018,376 B2 | 3/2006 | Webb et al. | |
| 7,027,557 B2 | 4/2006 | Liacer | |
| 7,044,602 B2 | 5/2006 | Chernyak | |
| 7,046,762 B2 | 5/2006 | Lee | |
| 7,046,765 B2 | 5/2006 | Wong et al. | |
| 7,070,327 B2 | 7/2006 | Collins | |
| 7,103,144 B2 | 9/2006 | Wong et al. | |
| 7,103,145 B2 | 9/2006 | Wong et al. | |
| 7,115,120 B2 * | 10/2006 | Lin | 606/4 |
| 7,139,601 B2 | 11/2006 | Bucholz et al. | |
| 7,154,991 B2 | 12/2006 | Earnst et al. | |
| 7,158,607 B2 | 1/2007 | Dilmanian et al. | |
| 7,158,610 B2 | 1/2007 | Mostafavi | |
| 7,166,852 B2 | 1/2007 | Saracen et al. | |
| 7,171,257 B2 | 1/2007 | Thomson | |
| 7,178,666 B2 | 2/2007 | Huang | |
| 7,179,254 B2 | 2/2007 | Pendekanti et al. | |
| 7,187,792 B2 | 3/2007 | Fu et al. | |
| 7,194,063 B2 | 3/2007 | Dilmanian et al. | |
| 7,204,640 B2 | 4/2007 | Fu et al. | |
| 7,221,733 B1 | 5/2007 | Takai et al. | |
| 7,225,012 B1 | 5/2007 | Susil et al. | |
| 7,227,925 B1 | 6/2007 | Mansfield et al. | |
| 7,231,076 B2 | 6/2007 | Fu et al. | |
| 7,239,684 B2 | 7/2007 | Hara et al. | |
| 7,260,426 B2 | 8/2007 | Schweikard et al. | |
| 7,266,176 B2 | 9/2007 | Allison et al. | |
| 7,278,787 B2 | 10/2007 | Hack et al. | |
| 7,280,865 B2 | 10/2007 | Adler | |
| 7,283,610 B2 | 10/2007 | Low et al. | |
| 7,346,144 B2 | 3/2008 | Hughes et al. | |
| 2002/0051513 A1 | 5/2002 | Pugachev et al. | |
| 2002/0065461 A1 * | 5/2002 | Cosman | 600/426 |
| 2002/0099363 A1 | 7/2002 | Woodward et al. | |
| 2002/0106054 A1 | 8/2002 | Caflisch et al. | |
| 2002/0106055 A1 | 8/2002 | Cash | |
| 2002/0115902 A1 | 8/2002 | Dejuan et al. | |
| 2002/0161356 A1 | 10/2002 | Bille et al. | |
| 2002/0198453 A1 * | 12/2002 | Herrick, II | 600/431 |
| 2002/0198553 A1 | 12/2002 | Schumer et al. | |
| 2003/0112922 A1 | 6/2003 | Burdette et al. | |
| 2003/0120141 A1 | 6/2003 | Adler | |
| 2003/0125622 A1 | 7/2003 | Schweikard et al. | |
| 2003/0189689 A1 | 10/2003 | Rathjen | |
| 2003/0211075 A1 | 11/2003 | Thorpe et al. | |
| 2003/0219098 A1 | 11/2003 | McNutt et al. | |
| 2004/0019274 A1 * | 1/2004 | Galloway et al. | 600/425 |
| 2004/0054359 A1 | 3/2004 | Ruiz et al. | |
| 2004/0071261 A1 | 4/2004 | Earl et al. | |
| 2004/0131150 A1 | 7/2004 | Pankratov et al. | |
| 2004/0267294 A1 | 12/2004 | Will | |
| 2005/0010109 A1 * | 1/2005 | Faul | 600/427 |
| 2005/0049478 A1 | 3/2005 | Kuduvalli et al. | |
| 2005/0180544 A1 * | 8/2005 | Sauer et al. | 378/195 |
| 2005/0192562 A1 | 9/2005 | Loesel et al. | |
| 2005/0203499 A1 | 9/2005 | Pendekanti et al. | |
| 2005/0226482 A1 | 10/2005 | Kuduvalli et al. | |
| 2005/0228255 A1 | 10/2005 | Saracen et al. | |
| 2005/0234327 A1 | 10/2005 | Saracen et al. | |
| 2005/0270486 A1 | 12/2005 | Teiwes et al. | |
| 2005/0271590 A1 | 12/2005 | Schwartz et al. | |
| 2006/0002601 A1 | 1/2006 | Fu et al. | |
| 2006/0002615 A1 | 1/2006 | Fu et al. | |
| 2006/0002630 A1 | 1/2006 | Fu et al. | |
| 2006/0002631 A1 | 1/2006 | Fu et al. | |
| 2006/0002632 A1 | 1/2006 | Fu et al. | |
| 2006/0004281 A1 | 1/2006 | Saracen | |
| 2006/0033044 A1 | 2/2006 | Gentry et al. | |
| 2006/0067469 A1 | 3/2006 | Dooley et al. | |

| | | |
|---|---|---|
| 2006/0072821 A1 | 4/2006 | Wang |
| 2006/0074292 A1 | 4/2006 | Thomson et al. |
| 2006/0074299 A1 | 4/2006 | Sayah |
| 2006/0074304 A1 | 4/2006 | Sayah |
| 2006/0078087 A1* | 4/2006 | Forman et al. ............. 378/65 |
| 2006/0084952 A1 | 4/2006 | Pallikaris et al. |
| 2006/0093089 A1 | 5/2006 | Vertatschitsch et al. |
| 2006/0170679 A1 | 8/2006 | Wang et al. |
| 2006/0176997 A1 | 8/2006 | Dilmanian et al. |
| 2006/0182326 A1 | 8/2006 | Schildkraut et al. |
| 2006/0192921 A1 | 8/2006 | Loesel et al. |
| 2006/0199991 A1 | 9/2006 | Lewis et al. |
| 2006/0203964 A1 | 9/2006 | Nyholm et al. |
| 2006/0271025 A1 | 11/2006 | Jones et al. |
| 2006/0274061 A1 | 12/2006 | Wang et al. |
| 2006/0274885 A1 | 12/2006 | Wang et al. |
| 2006/0274924 A1 | 12/2006 | West et al. |
| 2006/0274925 A1 | 12/2006 | West et al. |
| 2006/0291621 A1 | 12/2006 | Yan et al. |
| 2006/0291710 A1 | 12/2006 | Wang et al. |
| 2006/0293583 A1 | 12/2006 | Saracen et al. |
| 2007/0003007 A1 | 1/2007 | Carrano et al. |
| 2007/0003123 A1 | 1/2007 | Fu et al. |
| 2007/0015991 A1 | 1/2007 | Fu et al. |
| 2007/0038058 A1 | 2/2007 | West et al. |
| 2007/0053490 A1 | 3/2007 | Wang et al. |
| 2007/0071168 A1 | 3/2007 | Allison et al. |
| 2007/0071176 A1 | 3/2007 | Main et al. |
| 2007/0078306 A1 | 4/2007 | Allison et al. |
| 2007/0083087 A1 | 4/2007 | Carda |
| 2007/0093795 A1 | 4/2007 | Melcher et al. |
| 2007/0118010 A1 | 5/2007 | Hillstead et al. |
| 2007/0127622 A1 | 6/2007 | Main et al. |
| 2007/0127845 A1 | 6/2007 | Fu et al. |
| 2007/0140413 A1 | 6/2007 | Saracen |
| 2007/0169265 A1 | 7/2007 | Saracen et al. |
| 2007/0225691 A1 | 9/2007 | Silvestrini et al. |
| 2007/0225693 A1 | 9/2007 | Muehlhoff et al. |
| 2007/0249911 A1 | 10/2007 | Simon |
| 2008/0056434 A1 | 3/2008 | Grozinger et al. |
| 2008/0187099 A1* | 8/2008 | Gertner ................. 378/65 |
| 2008/0212738 A1* | 9/2008 | Gertner et al. ............. 378/65 |
| 2008/0317312 A1* | 12/2008 | Carl et al. ............... 382/131 |

FOREIGN PATENT DOCUMENTS

| | | |
|---|---|---|
| WO | WO 02/35996 | 5/2002 |
| WO | WO 2003/039370 | 5/2003 |
| WO | WO 2006/086631 | 8/2006 |
| WO | WO 2007/027164 | 3/2007 |

OTHER PUBLICATIONS

Georgopoulos, Michael et al., Tumour Regression of Uveal Melanoma after Ruthenium-106 Brachytherapy or Stereotactic Radiotherapy with Gamma Knife or Linear Accelerator, Ophthalmologica, 315-319 (2003).

Fakiris, Achilles J. et al., Gamma-Knife-Based Stereotactic Radiosurgery for Uveal Melanoma, Stereiotact. Funct. Neurosurg., 85:106-112 (2007).

Kirwan, James F. et al., Effect of βradiation on success of glaucoma drainage surgery in South Africa: randomized controlled trial, BMJ doi:10.1136/bmj.38971.395301.7C (Oct. 5, 2006).

Esquivel, Carlos Jr. et al., Novel low-kVp beamlet system for choroidal melanoma, Radiation Oncology I:36 (2006).

Kishi, Kazushi et al., Lead Contact Lens for Crystalline Lens Shielding in Electron Therapy for Eyelid Tumors, Radiation Medicine, vol. 14, No. 2, 107-109 (1996).

Bangerter, A. and Jager, L.; Forty Years' Experience with a Special, Non-Tumor Application of Radiotherapy for the Eye, European Journal of Medical Research, vol. 1 (1996), pp. 582-588.

Bailey, Edgar D., CHP, Chief Radiologic Health Branch, Syllabus on Radiography Radiation Protection, Filtration Regulatory Requirements, California Department of Health and Human Services, (2004), pp. 11-12.

Cornsweet, T.N. and Crane, H.D., Accurate Two-Dimensional Eye Tracker Using First and Fourth Purkinje, Journal of the Optical Society of America, 63(8), (1973). pp. 921-928.

Das, I. J., et al., Small Fields: Nonequilibrium Radiation Dosimetry, Medical Physics, 35(1) (2008), pp. 206-215.

Francescon, P., et al., Total Scatter Factors of Small Beams: A Multidetector and Monte Carlo Study, Medical Physics 35(2) (2008), pp. 504-513.

Jaywant, S. M., et al., Stereotactic Radiotherapy in the Treatment of Ocular Melanoma: A Noninvasive Eye Fixation Aid and Tracking System, Journal of Applied Clinical Medical Physics, vol. 4, No. 2 (2003), pp. 156-161.

Marcus, D. M., et al., External Beam Irradiation of Subfoveal Choroidal Neovascularization Complicating Age-Related Macular Degeneration, Arch Ophthalmology, vol. 119 (2001), pp. 171-180.

Marcus, D. M. and The AMDRT Research Group, The Age-Related Macular Degeneration Radiotherapy Trial (AMDRT): One Year Results from a Pilot Study, American Journal of Ophthalmology, vol. 138 (2004), pp. 818-828.

Sagerman, R. H. and Alberti, W. E., Radiation Techniques for the Treatment of Retinoblastoma and Orbital Tumors, Radiotherapy of Intraocular and Orbital Tumors, 2nd Revised Edition (2003), pp. 233-237.

Schilling, H. et al., Long Term Results After Low Dose Ocular Irradiation for Choroidal Haemangiomas, British Journal of Ophthalmology, vol. 81 (1997), pp. 267-273.

Schipper, J. and Tan, K.E., Management of Retinoblastoma by Precision Magevoltage Irradiation, Dept. of Radiation Therapy of the Univ. Hospital and the Royal Dutch Eye Hospital, Utrecht, The Netherlands (1983), pp. 534-540.

Sean, S. and Smit, E. F., Design of Clinical Trials of Radiation Combined with Antiangiogenic Therapy, The Oncologist, vol. 12, No. 4, (2007), pp. 465-477, www://theoncologist.alphamedpress.org.

Toma, N. M.G. et al., External Beam Radiotherapy for Retinoblastoma: II Lens Sparing Technique, British Journal of Ophthalmology, vol. 79 (1995), pp. 112-117.

Dieckmann et al., "A Linac-Based Stereotactic Irradiation Technique of Uveal Melanoma", Radiotherapy and Oncology, vol. 61, (2001), pp. 49-56.

Gao et al., "Orthovoltage radiation therapy treatment planning using Monte Carlo Simulation: treatment of neuroendocrine carcinoma of the maxillary sinus," ISSN: 0031-9155; vol. 42, No. 12., pp. 2421-2433 (1997).

Kobayashi et al., Radiotherapy for subfoveal neovascularization associated with pathological myopia: a pilot study., J. Ophth. 87:761-766 (2000).

Kim et al., "Combination hyperthermia and radiation therapy for malignant melanoma," Cancer, 50:478-482 (1982).

* cited by examiner

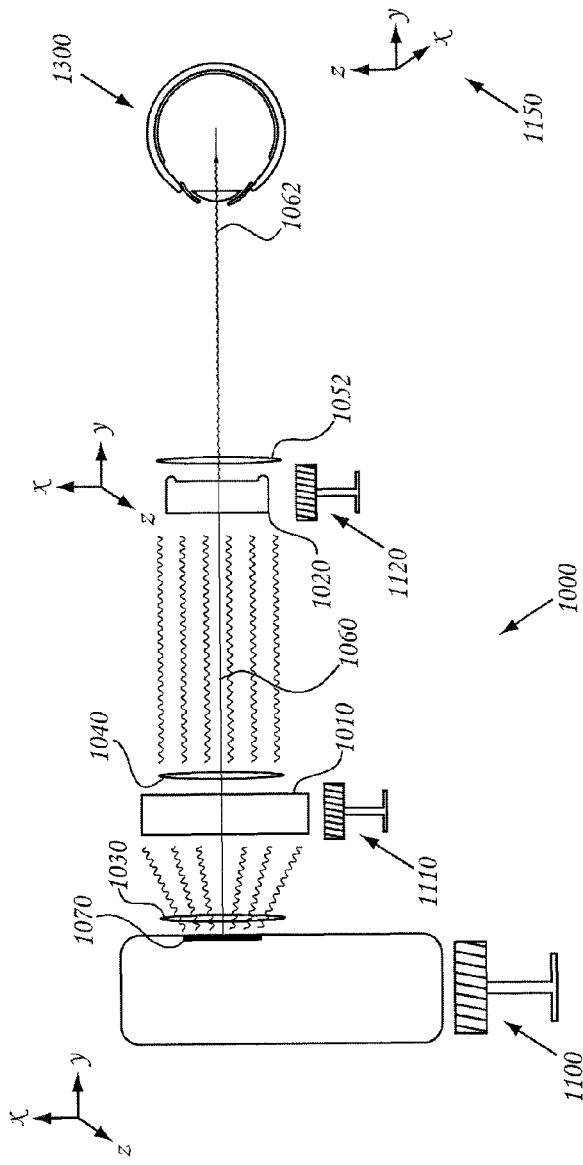
FIG. 2A
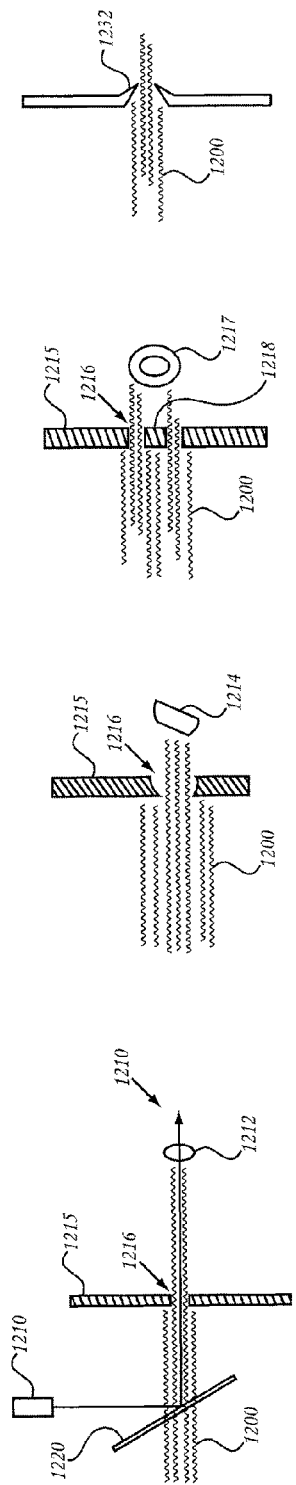
FIG. 2B'  FIG. 2B''  FIG. 2B'''  FIG. 2B''''

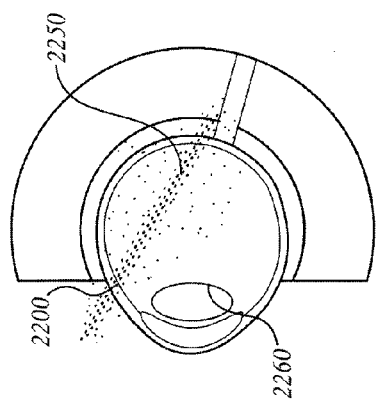
FIG. 7A Beam 1
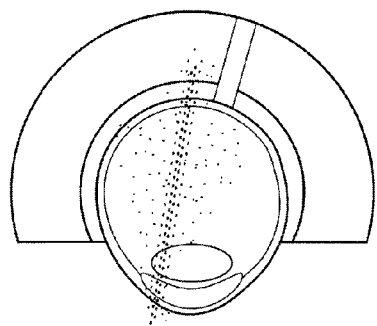
FIG. 7B Beam 2
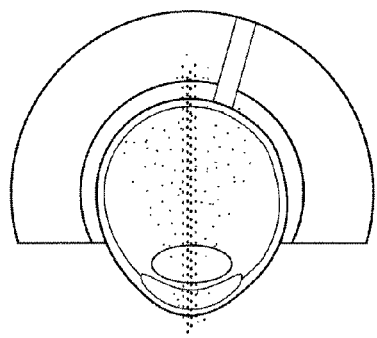
FIG. 7C Beam 3
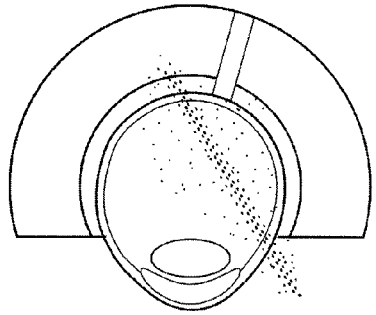
FIG. 7D Beam 4
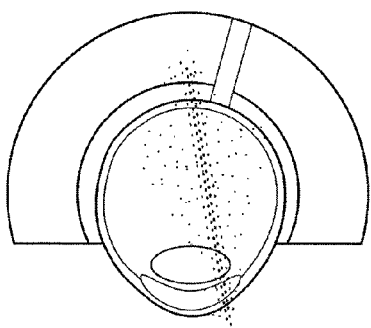
FIG. 7E Beam 5

PORTABLE ORTHOVOLTAGE RADIOTHERAPY

RELATED APPLICATIONS

This application claims priority benefit of U.S. Provisional Application No. 60/933,220, filed Jun. 4, 2007, entitled, "PORTABLE ORTHOVOLTAGE RADIOTHERAPY"; U.S. Provisional Application No. 60/922,741, filed Apr. 9, 2007, entitled, "RADIATION THERAPY SYSTEM FOR THE TREATMENT OF MACULAR DEGENERATION"; U.S. Provisional Application No. 60/869,872, filed Dec. 13, 2006, entitled, "XRAY TREATMENT SYSTEM"; U.S. Provisional Application No. 60/862,210, filed Oct. 19, 2006, entitled, "METHODS AND DEVICE FOR NON-INVASIVE ROBOTIC TARGETING OF INFLAMMATORY LESIONS USING RADIATION"; U.S. Provisional Application No. 60/862,044, filed Oct. 18, 2006, entitled, "METHODS AND DEVICES FOR NON-INVASIVE ROBOTIC TARGETING OF RETINAL LESIONS"; and U.S. Provisional Application No. 60/829,676, filed Oct. 16, 2006, entitled, "METHODS AND DEVICES TO APPLY FOCUSED ENERGY TO BODY REGIONS"; the entirety of each of which are incorporated herein by reference.

BACKGROUND

1. Field of the Inventions

This disclosure relates to the treatment of ocular disorders using targeted photon energy. In particular, the present disclosure relates to an apparatus, systems, and methods for image-guided low energy x-ray therapy of ocular structures.

2. Description of the Related Art

Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused or results in an inflammatory process which ultimately causes destruction of the retina. The inflammatory process can result in direct destruction of the retina or destruction via formation of neovascular membranes which leak fluid and blood into the retina, quickly leading to scarring.

Most treatments for macular degeneration are aimed at stopping the neovascular (or "wet") form of macular degeneration rather than geographic atrophy, or the "dry" form of Age-related Macular Degeneration (AMD). All wet AMD begins as dry AMD. Indeed, the current trend in advanced ophthalmic imaging is that wet AMD is being identified prior to loss of visual acuity. Treatments for macular degeneration include the use of medication injected directly into the eye (Anti-VEGF therapy), laser therapy in combination with a targeting drug (photodynamic therapy); other treatments include brachytherapy (the local application of a material which generates beta-radiation).

SUMMARY

It would be advantageous to provide a treatment for ocular disorders which irradiates specific regions of the eye without substantially exposing the rest of the eye to radiation. In some embodiments described herein, a radiotherapy system is disclosed that may be used to treat a wide variety of medical conditions relating to the eye. For example, the system may be used, alone or in combination with other therapies, to treat macular degeneration, diabetic retinopathy, inflammatory retinopathies, infectious retinopathies, tumors in the eye or around the eye, glaucoma, refractive disorders, cataracts, post-surgical inflammation of any of the structures of the eye, ptyrigium, and dry eye.

In some embodiments described herein, radiotherapy (or externally applied radiation therapy) is used for treatment of macular degeneration, and a standard treatment for macular degeneration is disclosed. Radiotherapy for treatment of macular degeneration presents several complications. For example, the eye contains several critical structures, such as the lens and the optic nerve, that can possibly be damaged by excessive exposure to radiation. The application of external beam therapy is limited by devices and methodologies used to apply the therapy. These devices and methodologies are older radiation technologies used to treat conditions such as tumors anywhere in the body and were not developed specifically for ocular radiation therapy. In addition, logistics are difficult as far as patient recruitment and administration of treatments because such treatment devices are borrowed from and displace oncologic therapies.

Retinal radiotherapy trials have shown stabilized or improved visual acuity without any significant toxicity. Radiation has also been shown to dry up neovascular membranes in patients and stabilize vision. However, due to limitations in the treatment of macular degeneration using radiotherapy including localization of the region to be treated as well as specific application of the radiation to the region to be treated, retinal radiotherapy often irradiates the entire retina, which is both unnecessary and possibly harmful.

Brachytherapy for wet AMD is also a powerful therapy to treat wet AMD (Neovista, Inc., Press Release, March 2007, the entirety of which is incorporated herein by reference). A major limitation of this treatment is that it requires invasive procedures involving partial removal of the vitreous fluid of the posterior chamber of the eye to place the brachytherapy probe. In addition, it cannot be fractionated because of the invasiveness required to deliver it. Furthermore, it would be difficult to apply this therapy to patients who do not yet have vision loss because of the potential complications from the procedure.

Other diseases of the eye include glaucoma. In this disease, surgery is often the second line of therapy after pharmaceutical therapy. Procedures such as trabeculoplasty, trabeculotomy, canaloplasty, laser iridotomy, placement of shunts, and other procedures all suffer from a short-lived effect because of scar formation as a result of the surgical trauma. Anti-inflammatory drugs appear to offer a palliative and/or preventative solution to the chronic scarring that occurs after these procedures; however, the drugs have to be given several times per day and are associated with their own side effect profile such as seepage into unwanted regions of the eye. Radiation (10 Gy) can be beneficial in the prevention of scarring after glaucoma surgery (Kirwan, et. al., Effect of Beta Radiation on Success of Glaucoma Drainage Surgery in South Africa: randomized controlled trial; British Medical Journal, Oct. 5, 2006, the entirety of which is herein incorporated by reference). Capsular opacification is a common occurrence after cataract procedures with placement of intra-ocular lenses. This scarring is caused by trauma from the surgery, proliferation of lens cells, and material incompatibility.

In some embodiments, the radiation treatment system is used concomitantly with laser therapy. That is, rather than using a laser solely for pointing the x-ray device to the ocular target of choice, the laser is used for both pointing and therapy. In these embodiments, the laser preferably includes at least one additional energy or wavelength suitable for therapy of an ocular structure. The x-ray is preferably applied to the same region as the laser so as to prevent excessive scarring around the laser therapy.

In some embodiments of this disclosure, the electromotive and ocular imaging systems are utilized but laser therapy is the sole radiation energy source used for treatment. In this embodiment, the ability of the system to focus radiation by passing the photons through the sclera from different angles to structures deep to the sclera can be utilized to treat diseases of the anterior chamber or posterior chamber with laser radiation while keeping the x-ray generation system off, indeed in some embodiments of the system, the x-ray generator is not included in the system. In these embodiments, the eye model, tracking, control, and focusing systems for the x-ray therapy are utilized for therapeutic laser therapy.

In certain embodiments, a device using a treatment planning system is disclosed for providing targeted radiotherapy to specific regions of the eye. The treatment planning system integrates physical variables of the eye as well as disease variables from the physician to direct the x-ray system to deliver therapy to the ocular structures. The device applies narrow beams of radiation from one or more angles to focus radiation to a targeted region in or on the eye. In certain embodiments, the device may focus radiotherapy to structures of the posterior eye, such as the retina. In certain embodiments, the device may focus radiotherapy to structures of the anterior region of the eye, such as the sclera. The treatment planning system allows for planning of the direction of the beam entry into the eye at different points along the sclera. The unique anatomy of each individual is integrated into the treatment planning system for accurate targeting, and in some examples, automated positioning of the x-rays of the device.

In some embodiments described herein, a treatment system is provided for delivering radiation to a patient. The system preferably includes an eye model derived from anatomic data of a patient's eye, an emitter that emits a radiation beam, and a position guide, coupled to the emitter, that positions, based on the eye model, the emitter with respect to a location on or in the eye, such that the radiation beam is delivered to a target on or in the eye.

In some embodiments, the location comprises the target. The emitter can be configured to deliver the radiation beam with a photon energy between about 10 keV and about 500 keV or to deliver an radiation beam adjustable between about 25 keV and about 100 keV. In some embodiments, the radiation beam includes an x-ray beam. In some embodiments, the system further includes a planning module configured to determine, based on the eye model, at least two of a beam target, a beam intensity, a beam energy, a beam trajectory, a treatment field size, a treatment field shape, a distance from the emitter to the target, an exposure time, and a dose.

The position guide, in some embodiments, positions the emitter, based on information from the planning module, such that the emitter directs a first radiation beam at a first position through a first portion of the eye to a treatment region within the eye. The position guide preferably positions the emitter, based on information from the planning module, such that the emitter directs a second radiation beam at a second position through a second portion of the eye to the treatment region within the eye. In some embodiments, the planning module is adapted to receive input from a user, the input affecting an output of the planning module. In some embodiments, the system includes a sensing module that senses a position of the eye and relays information concerning the position of the eye to the planning module.

The system includes, in some embodiments, a sensing module that senses a position of the eye and relays information concerning the position of the eye to the position guide. The sensing module can include a portion that physically contacts the eye, which can include a lens positionable on or over the cornea of the eye. The sensing module can, in some embodiments, optically sense the position of the eye with, for example, a laser.

In some embodiments, the system also includes a collimator that collimates the radiation beam to a width of from about 0.5 mm to about 6 mm. The collimated beam can also have a penumbra of less than about ten percent at a distance up to about 50 cm from the collimator. The position guide, in some embodiments, is configured to position the emitter, in use, at a first distance within 50 cm of the target, such that the emitter delivers the radiation beam to the target from the first distance. In some embodiments, a collimator is positioned, in use, to within about 10 cm of the target when the radiation beam is delivered to the target.

The system can further include a detector that detects if the patient's eye moves such that the radiation beam is not directed to the target. In some embodiments, the emitter is configured to automatically not emit the radiation beam if the patient's eye moves out of a predetermined position or range of positions. Some embodiments include a laser emitter that emits a laser beam that passes through a collimator and is directed toward the eye.

Some embodiments described herein disclose a system for delivering radiation to an eye that includes an eye model derived from anatomic data of a patient's eye, an emitter that delivers an x-ray beam to the eye with an energy from about 10 keV to about 500 keV, a position guide, coupled to the emitter, that positions, based on the eye model, the emitter with respect to a location in or on the eye, to deliver the x-ray beam to a target in or on the eye, and a planning module that determines at least two parameters of treatment based on the model of the eye. In some embodiments, the at least two parameters include two of a beam target, a beam intensity, a beam energy, a beam trajectory, a treatment field size, a treatment field shape, a distance from the emitter to the target, an exposure time, and a dose.

The position guide, in some embodiments, is configured to direct a first x-ray beam from a first position to a first region of a sclera of the eye to target a region of the eye, and is further configured to direct a second x-ray beam from a second position to a second region of the sclera to target substantially the same region of the eye. In some embodiments, the region of the eye is at least one of the macula, the sclera, the trabecular meshwork, and a capsule of the lens of the eye.

The system can further include a collimator that collimates the x-ray beam. In some embodiments, the collimator is configured to collimate the x-ray beam to a width of from about 0.5 mm to about 6 mm, and in some embodiments, the system is configured to produce an x-ray beam having a penumbra of less than about five percent within a distance, from the collimator to the target, of about 50 cm. The emitter, in some embodiments, is configured to deliver an x-ray beam with a photon energy between about 25 keV and about 150 keV. In some embodiments, the collimator is positioned, in use, to within about 10 cm of the target when the x-ray beam is delivered to the target.

In some embodiments, a treatment system for delivering radiation to a human being is provided, the system including an eye model derived from anatomic data of a patient's eye; an emitter that delivers an x-ray beam to the eye; and means for positioning the emitter, with respect to a location on or in the eye, to deliver the x-ray beam to a target on or in the eye, the means being coupled to the emitter, and the positioning of the emitter being based on the eye model.

Some embodiments provide a treatment system for delivering radiation to a patient that includes an emitter that generates an radiation beam, and a position guide, coupled to the emitter, operable to positions the emitter with respect to a location on or in the eye, to deliver the radiation beam to a target on or in the eye, wherein the emitter is placed within 50 cm of the target. In some embodiments, the system further includes a collimator coupled to the emitter, the collimator being placed, in use, to within 10 cm of the target when the emitter emits the radiation beam. In some embodiments, the system further includes a collimated laser emitter that is coupled to the emitter.

In some embodiments described herein, a method of treating macular degeneration of an eye is disclosed. The method preferably includes providing a model of an eye of a patient with anatomic data obtained by an imaging apparatus, producing an x-ray beam with a width of from about 0.5 mm to about 6 mm and having a photon energy between about 40 keV and about 100 keV, and in some embodiments between about 40 keV and about 250 keV, directing the x-ray beam such that the beam passes through the sclera to the retina of the eye, and exposing the retina to from about 1 Gy to about 40 Gy of x-ray radiation.

In some embodiments, the method provides that at least one of the x-ray beam width, photon energy, and direction of the x-ray beam is determined based on the model of the eye. The method further provides, in some embodiments, that the retina is exposed to from about 15 Gy to about 25 Gy of x-ray radiation. In some embodiments, treatment with the x-ray radiation can be fractionated, and a planning system can keep track of the quantity and location of prior treatments. In some embodiments, the method includes reducing neovascularization in the eye by exposing the retina to the radiation. The method may further include administering to the patient at least one of heating, cooling, vascular endothelial growth factor (VEGF) antagonist, a VEGF-receptor antagonist, an antibody directed to VEGF or a VEGF receptor, microwave energy, laser energy, hyperbaric oxygen, supersaturate oxygen, ultrasound energy, radiofrequency energy, and a therapeutic agent, prior to, or after, exposing the retina to the radiation. The method further includes, in some embodiments, directing a first x-ray beam to pass through the sclera to the retina from a first position external to the eye, and directing a second x-ray beam to pass through the sclera to the retina from a second position external to the eye. In some embodiments, the x-ray beam is directed to pass through a pars plana of the eye. The x-ray beam is, in some embodiments, directed to a macula of the eye.

Some embodiments herein describe a method of treating an eye of a patient that includes providing a model of the eye based on anatomic data obtained by an imaging apparatus, producing a first x-ray beam and a second x-ray beam, each beam having a width of from about 0.5 mm to about 6 mm, directing the first x-ray beam such that the first beam passes through a first region of a sclera of the eye to a target of a retina, and directing the second x-ray beam such that the second beam passes through a second region of the sclera to substantially the same target of the retina as the first beam, wherein the first region and second region of the sclera through which the first beam and second beam pass are selected based on the model of the eye.

In some embodiments, a trajectory of the first beam is determined based on the model of the eye, and in some embodiments, the directing of the first x-ray beam and the directing of the second x-ray beam occur sequentially. In some embodiments, the first x-ray beam and the second x-ray beam have photon energies of from about 25 keV to about 100 keV. Centers of the first and second x-ray beams, in some embodiments, are projected through a point on the sclera at a distance of from about 0.5 mm to about 6 mm from a limbus of the eye. In some embodiments, the method further includes administering to the patient at least one of heating, cooling, VEGF antagonist, a VEGF-receptor antagonist, an antibody directed to VEGF or a VEGF receptor, microwave energy, radiofrequency energy, laser energy, and a therapeutic agent, prior to, concurrently with, or subsequent to the directing of the first x-ray beam. The x-ray beam, in some embodiments, is produced by an x-ray source positioned less than about 50 cm from the retina. In some embodiments, the x-ray beam is emitted from a source having an end that is placed within about 10 cm of the eye. In some embodiments, the retina is exposed to about 15 Gy to about 25 Gy in some embodiments, and, in some embodiments to about 35 Gy, of x-ray radiation during one treatment session.

Some embodiments described herein relate to a method of treating an eye of a patient that includes providing a model of the eye based on anatomic data obtained by an imaging apparatus, producing a first x-ray beam and a second x-ray beam, each beam having a width of from about 0.5 mm to about 6 mm, directing the first x-ray beam such that the first beam passes through a first region of the eye to a target within the eye, and directing the second x-ray beam such that the second beam passes through a second region of the eye to substantially the same target within the eye, wherein the first region and second region of the eye through which the first beam and second beam pass are selected based on the model of the eye.

The target, in some embodiments, includes the lens capsule of the eye. In some embodiments, the target includes the trabecular meshwork of the eye or a tumor. In some embodiments, the first region comprises the cornea of the eye. In some embodiments, the first x-ray beam and the second x-ray beam have photon energies of from about 25 keV to about 100 keV. In some embodiments, the first and second x-ray beams are collimated by a collimator positioned within 10 cm of the eye, and in some embodiments, the x-ray beams are produced by an x-ray source positioned within 10 cm of the eye. The x-ray source can also be positioned within 50, 40, and/or 10 cm of the eye.

In some embodiments, the first region of the eye includes a first region of a sclera and the second region of the eye comprises a second region of the sclera, and an edge-to-edge distance from the first region of the sclera to the second region of the sclera is from about 0.1 mm to about 2 mm. In some embodiments, the first and second x-ray beams are directed from a nasal region external to the eye. Some methods further include aligning the center of the patient's eye with the x-ray radiotherapy system. Some methods also include developing a plan to treat a macular region using the model of the eye, wherein the first and second x-ray beams overlap at the macular region, and the first and second x-ray beams are collimated to from about 0.5 mm to about 6 mm.

Some embodiments described herein disclose a method of applying radiation to the retina of a patient's eye, the method including localizing the macula of the patient with an imaging device, linking the macula to a global coordinate system, and applying an external beam of radiation to the macula based on the coordinate system.

Some embodiments described herein disclose methods, of applying radiation to a patient's eye, that include obtaining imaging data of at least a portion of a patient's eye; identifying, based on the imaging data, a location of a macula of the patient's eye; identifying a first location of a fiducial marker located in or on the eye; mapping the location of the macula, relative to the first location of the fiducial marker, in a coordinate system, thereby producing a mapped location of the macula in the coordinate system; positioning, based on the mapped location of the macula, a radiation source that applies radiation to the macula; and emitting the radiation from the positioned radiation source to the macula.

In some embodiments, a contact lens that contacts the sclera and/or the cornea of the patient comprises the fiducial marker. The positioning of the radiation source is automated, in some embodiments, based on the coordinate system. The methods may also include repositioning the radiation source based on a movement of the fiducial marker to a second location of the fiducial marker. In some embodiments, the methods include, after the repositioning of the radiation source, emitting an additional radiation beam from the radiation source to the macula.

In certain embodiments, after mapping the location of the macula, methods include detecting a movement of the eye. The methods also may include determining a relative relationship between a new location of the macula and the coordinate system after the detecting of the eye movement. Some embodiments further include relaying information about the new location of the macula to a positioner that changes a position of the radiation source, and in some embodiments, applying the radiation to a region of drusen in the eye.

In some embodiments, the emitting the radiation comprises emitting a radiation beam. Some embodiments further include applying at least one additional radiation beam to the macula. In some embodiments, the radiation beam and the at least one additional radiation beam are applied simultaneously. In certain embodiments, the radiation beam and the at least one additional radiation beam are directed such that they intersect within a volume of tissue that includes the macula. The obtaining imaging data of the retina, in some embodiments, includes at least one of triangulation, interferometry, and phase shifting. In some embodiments, the imaging data is obtained with at least one of computed tomography, magnetic resonance imaging, optical coherence tomography, and positron emission tomography.

Described herein are methods, of applying radiation to a patient's eye, that include obtaining imaging data of at least a portion of a patient's eye; identifying, based on the imaging data, a location of a macula of the patient's eye; identifying a first location of an anterior structure of the eye; mapping the location of the macula, relative to the first location of the anterior structure of the eye, in a coordinate system, thereby producing a mapped location of the macula in the coordinate system; positioning, based on the mapped location of the macula in the coordinate system, a radiation source to apply a dose of radiation to the macula; and emitting a radiation beam from the positioned radiation source to the macula.

In certain embodiments, the anterior structure of the eye includes the sclera, and in some embodiments, the anterior structure of the eye includes at least one of a cornea, an anterior chamber, an iris, a conjunctiva, a pupil, an iridocorneal angle, a trabecular meshwork, a lens capsule, a prosthetic intraocular lens, a ciliary body, a ciliary muscle, a limbus, a pars plana, a scleral spur, and a lens of the eye.

Some embodiments further include repositioning the radiation source based on a movement of the anterior structure to a second location of the anterior structure. Certain embodiments further include, after the repositioning of the radiation source, emitting an additional radiation beam from the radiation source to the macula. In some embodiments, obtaining imaging data of the retina includes at least one of triangulation, interferometry, and phase shifting.

Some embodiments provide a method of treating a region of an eye of a patient that includes producing an x-ray beam with a width of from about 0.5 mm to about 6 mm and having a photon energy between about 40 keV and about 250 keV, directing the x-ray beam toward the eye region, and exposing the region to a dose of from about 1 Gy to about 40 Gy of x-ray radiation, thereby treating the region of the eye.

In some embodiments, the method further includes providing a model of the eye with anatomic data obtained by an imaging apparatus, wherein at least one of a width of the x-ray beam, a photon energy of the x-ray beam, and a direction of the x-ray beam is determined based on the model of the eye. The region, in some embodiments, is exposed to from about 15 Gy to about 25 Gy of x-ray radiation, and in some embodiments, the region includes a retina of the eye. The treating can include reducing neovascularization in the eye by exposing the retina to the radiation, and/or substantially preventing progression from Dry Age-related Macular Degeneration (AMD) to neovascularization. In some embodiments, the method also includes administering to the patient at least one of heating, cooling, VEGF antagonist, a VEGF-receptor antagonist, an antibody directed to VEGF or a VEGF receptor, microwave energy, radiofrequency energy, a laser, a photodynamic agent, and a radiodynamic agent, and a therapeutic agent. Some embodiments further include directing a first x-ray beam to pass through a sclera to a retina from a first position external to the eye, and directing a second x-ray beam to pass through the sclera to the retina from a second position external to the eye. The x-ray beam, in some embodiments, is directed through a pars plana of the eye, and in some embodiments, the x-ray beam is directed to a macula of the eye. The x-ray beam can also be directed through a sclera of the eye to the macula of the eye.

Some embodiments provide that the dose is divided between two or more beams, and in some embodiments, the dose is divided between two or more treatment sessions, each of said treatment sessions occurring at least one day apart. Some methods described herein further include determining a position of the eye relative to the x-ray beam during the exposing of the region to the x-ray radiation, and shutting off the x-ray beam if the position of the eye exceeds a movement threshold.

Some methods of treating an eye of a patient described herein include providing a model of the eye based on anatomic data obtained by an imaging apparatus, directing a first x-ray beam such that the first beam passes through a first region of the eye to a target within the eye, and directing a second x-ray beam such that the second beam passes through a second region of the eye to substantially the same target within the eye, wherein the first region and second region of the eye through which the first beam and second beam pass are selected based on the model of the eye, and assessing a position of the eye during at least one of the administration of the first x-ray beam to the target, administration of the second x-ray beam to the target, and a period of time between administration of the first x-ray beam to the target and administration of the second x-ray beam to the target.

Some methods provide that the assessing occurs during administration of the first x-ray beam to the target, and some methods further include ceasing or reducing administration of the first x-ray beam when the eye moves beyond a movement threshold. Some methods further include directing the second x-ray beam based on information from the assessing of the position of the eye.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 2A illustrates a side schematic view of embodiments of a radiotherapy system illustrating some system components of FIGS. 1A-B.

FIGS. 2B'-2B"" illustrate several embodiments of various collimators.

FIGS. 7A-7F illustrates representative simulations of radiation beams traveling through an eye to reach a retina of the eye and a dose profile for a target tissue.

DETAILED DESCRIPTION

Figure 1A:
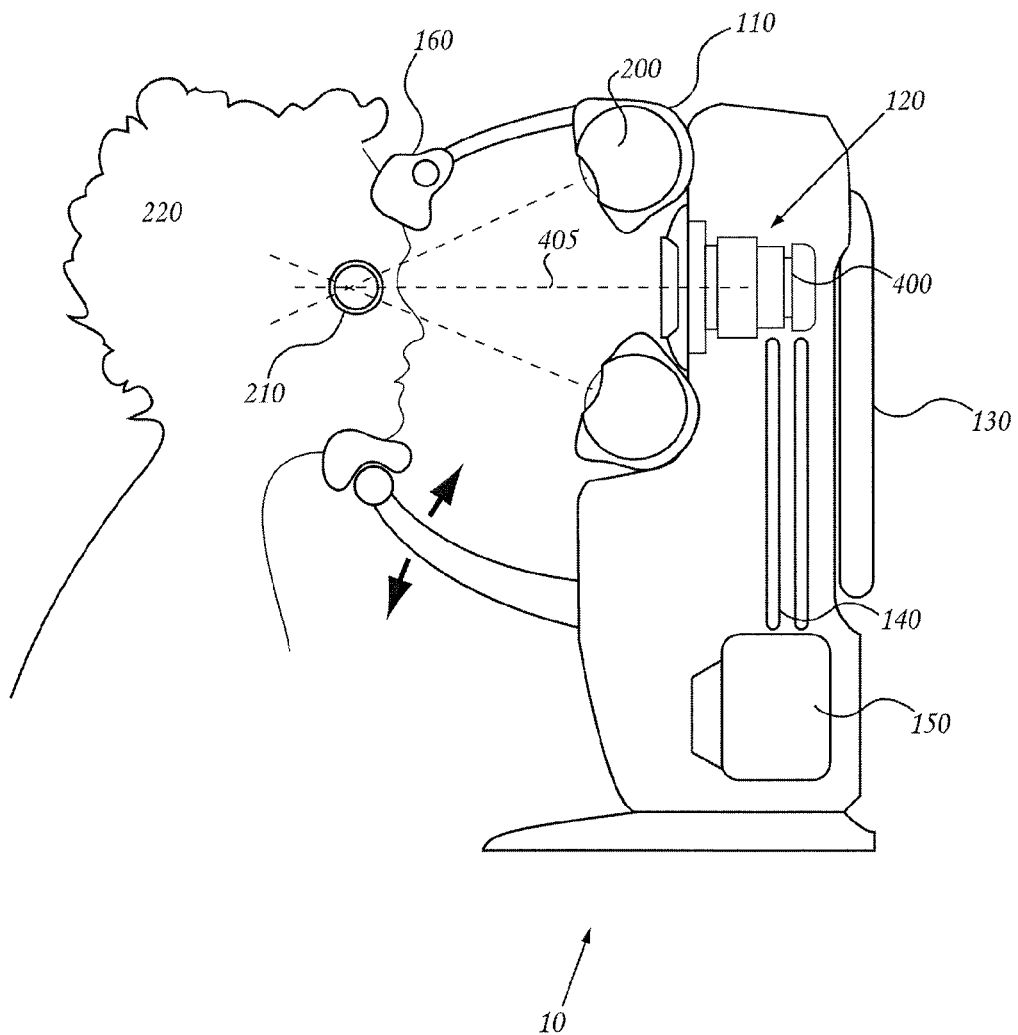
FIG. 1A illustrates a side view of embodiments of a system for treating the eye using radiotherapy.

The present embodiments include systems and methods for treating a human eye with radiotherapy. Some embodiments described below relate to systems and methods for treating macular degeneration of the eye using radiotherapy. For example, in some embodiments, systems and methods are described for use of radiotherapy on select portions of the retina to impede or reduce neovascularization of the retina. Some embodiments described herein also relate to systems and methods for treatment of glaucoma or control wound healing using radiotherapy. For example, in some embodiments, systems and methods are described for use of radiotherapy on tissue in the anterior chamber following glaucoma surgery, such as trabeculoplasty, trabeculotomy, canaloplasty, and laser iridotomy, to reduce the likelihood of postoperative complications. In other embodiments, systems and methods are described to use radiotherapy to treat drusen, inflammatory deposits in the retina that are thought to lead to vision loss in macular degeneration. Localization of a therapy to the drusen to treat the surrounding inflammation may prevent the progression of dry and/or wet AMD. Alternatively, a laser therapeutic is applied to the drusen in combination (adjuvant therapy) with co-localized x-ray radiation to substantially the same spot where the laser touched down on the retina; the laser spot can create a localized heating effect which can facilitate radiation treatment or the laser spot can ablate the region and the radiation can prevent further scarring around the laser spot. Such combination therapy can enhance the efficacy of each therapy individually. Similarly, adjuvant therapies can include x-ray radiotherapy in combination with one or more pharmaceuticals or other radiotherapy enhancing drugs or chemical entities.

Radiation can have both a broad meaning and a narrow meaning in this disclosure. Radiation, as used herein, is intended to have its ordinary meaning and is meant to include, without limitation, at least any photonic-based electromagnetic radiation which covers the range from gamma radiation to radiowaves and includes x-ray, ultraviolet, visible, infrared, microwave, and radiowave energies. Therefore, planned and directed radiotherapy can be applied to an eye with energies in any of these wavelength ranges.

Radiotherapy can refer to treatment of disease using x-ray radiation; however, in this disclosure, radiotherapy is intended to have its ordinary meaning and is meant to include, without limitation, at least any type of electromagnetic radiation which uses photons to deliver an energy as a clinical therapy to treat a disease. X-ray radiation generally refers to photons with wavelengths below about 10 nm down to about 0.01 nm. Gamma rays refer to electromagnetic waves with wavelengths below about 0.01 nm. Ultraviolet radiation refers to photons with wavelengths from about 10 nm to about 400 nm. Visible radiation refers to photons with wavelengths from about 400 nm to about 700 nm. Photons with wavelengths above 700 nm are generally in the infrared radiation regions. Within the x-ray regime of electromagnetic radiation, low energy x-rays can be referred to as orthovoltage. While the exact photon energies of orthovoltage varies, for the disclosure herein, orthovoltage refers at least to x-ray photons with energies from about 20 KeV to about 500 MeV.

The global coordinate system refers to a physical world of a machine or room. The global coordinate system is preferably a system relating a machine, such as a computer or other operating device, to the physical world or room that is used by the machine. The global coordinate system can be used, for example, to move a machine, components of a machine, or other things from a first position to a second position. The global coordinate system can also be used, for example, to identify the location of a first item with respect to a second item. In some embodiments, the global coordinate system is based on a one-dimensional environment. In some embodiments, the global coordinate system is based on a two-dimensional environment, and in some embodiments, the global coordinate system is based on three or more dimensional environments.

Kerma, as used herein, refers to the energy released (or absorbed) per volume of air when the air is hit with an x-ray beam. The unit of measure for Kerma is Gy. Air-kerma rate is the Kerma (in Gy) absorbed in air per unit time. Similarly, "tissue kerma" rate is the radiation absorbed in tissue per unit time. Kerma is generally agnostic to the wavelength of radiation, as it incorporates all wavelengths into its joules reading.

The beam shape is generally set by the last collimator opening in the x-ray path; with two collimators in the beam path, the secondary collimator is the last collimator in the beam path and can be called the "shaping collimator." The first collimator may be called the primary collimator because it is the first decrement in x-ray power and generally is the largest decrement of the collimators; the second collimator can generally set the final shape of the x-ray beam. As an example, if the last collimator opening is a square, then the beam shape is a square as well. If the last collimator opening is circular, then the beam is circular. In some embodiments, there is one collimator which serves as the primary collimator as well as the beam shaping collimator.

The penumbra refers to the fall-off in dose outside of the area of the last collimator and beam shape and size set by that collimator, typically measured at some distance from the last collimator. Penumbra, as used herein, has its ordinary meaning, which is meant to include, without limitation, the percentage of radiation outside the area of the last collimator when the x-ray beam reaches the surface of the eye or the target within the eye, whichever structure is the one being referenced with respect to the penumbra. The penumbra can incorporate the divergence of the beam as well as the scatter of the beam as it travels through the air and through the tissue.

Ideally, the size of the primary beam is the same size as the last collimator to which the x-ray beam is exposed; that is, the penumbra is ideally zero. In reality, a penumbra of zero is difficult to achieve when the collimator is any distance from the target. However, the penumbra can be optimized, for example, by the shape of the collimator, the material of the collimator, the processing of the collimator material, the position of the anode of the x-ray tube, and the relative sizing of the collimator relative to the x-ray source. In some embodiments of the systems and methods provided herein, the penumbra area percentage at the entry point to the eye is less than about 10%. In some embodiments, the penumbra area percentage at the entry point to the eye is less than about 5%, and in some embodiments, the penumbra area percentage is less than about 1%.

The penumbra can also refer to the percentage of radiation outside the zone of the shaping collimator at a target region of the macula. In some embodiments, the penumbra at the macula is less than about 40% and in some embodiments, the penumbra at the macula is less than about 20%, and in some embodiments, the penumbra at the macula is less than about 10% or less than about 5%. The penumbra can be incorporated into a treatment plan; for example, predictive knowledge of the penumbra can be utilized to plan the treatment. In one example, a finely collimated beam (e.g., having a 4 mm diameter) is applied to the sclera. The beam at the retina can be 5 mm (25% penumbra) or 6 mm (50% penumbra) diameter sufficient for coverage of a lesion. With this method, the structures of the anterior eye are minimally irradiated while the lesion at the retina is fully covered. In this embodiment, divergence of the x-ray beam is utilized for minimizing the exposure of the front of the eye without sacrificing a therapeutic dose to the retina.

A related definition is that of "isodose fall-off" which refers to the dose fall-off independent of divergence angle of the beam. For example, in an ideal setting where there is no divergence angle, the isodose fall off is the same as penumbra. When divergence angle is introduced, the isodose fall-off is different from the penumbra, referring to the fall-off of dose around the shaping collimator beam without accounting for divergence angle. The isodose fall off is measured in Gy/mm, a linear distance from the edge of the collimator shape over a distance. Divergence angles typically follow a $1/R^2$ relationship assuming the source is a point source or close to a point source. Divergence angle is highly predictable for photons and can be calculated independently of scatter and the other physics which go into Monte Carlo simulations.

Photons with shorter wavelengths correspond to radiation with higher energies. The higher-energy range of x-rays is generally in the MeV range and is generally referred to gamma x-rays, independent of how the radiation was generated. X-ray photons with relatively shorter wavelengths are referred to as orthovoltage x-rays. Higher energy radiation with shorter wavelengths corresponds to deeper penetration into target tissue, which is the reason that most applications using MeV energies require extensive shielding of the patient and surroundings. In some embodiments of this disclosure, x-rays typically used for diagnostic purposes, or low energy orthovoltage x-ray sources, can be used for therapy of ocular diseases and/or disorders which are relatively superficial in the patient such as breast, intra-operative radiation application, skin cancers, and other disorders such as peripheral vascular disease, implants, etc. X-rays typically used for diagnosis can be used for therapy by tightly collimating the x-ray beam into a thin beam of x-ray photons and directing the beam to the superficial region to be treated. If the disorder is deeper than several centimeters inside the body, then higher energy sources (e.g., MeV) may be preferred to enhance penetration of energy to the disorders. It is difficult to collimate MeV x-ray beams to small diameters with small penumbras because their very high speed photons cause secondary interactions with tissue including generation of secondary x-rays and other radiations. X-rays with energies lower than 500 KeV and even lower than 200 KeV can more appropriately be collimated to very small diameters.

"Laser" energy is also composed of photons of different energies ranging from short wavelengths, such as ultraviolet radiation, up to long wavelengths, such as infrared radiation. Laser refers more to the delivery mechanism than to the specific wavelength of radiation. Laser light is considered "coherent" in that the photons travel in phase with one another and with little divergence. Laser light is also collimated in that it travels with relatively little divergence as is proceeds in space (penumbra). Light can be collimated without being coherent (in phase) and without being a laser; for example, lenses can be used to collimate non-x-ray light. X-ray light is typically collimated with the use of non-lens collimators, the penumbra defining the degree of successful collimation. Laser pointers are typically visualization tools, whereas larger, higher-flux lasers are utilized for therapeutic applications. In some embodiments, optics can be used, such as lenses or mirrors, and in some embodiments, there are no intervening optical elements, although collimators may be used.

The two eye chambers are the anterior and posterior chambers. The anterior chamber includes the lens, the conjunctiva, the cornea, the sclera, the trabecular apparatus, the ciliary bodies, muscles, and processes, the iris, etc. The posterior chamber includes the vitreous humor, the retina, and the optic nerve.

"Ocular diseases," as used in this disclosure, is intended to have its ordinary meaning, and is meant to include at least disease of the anterior eye (e.g., glaucoma, presbyopia, cataracts, dry eye, conjunctivitis) as well as disease of the posterior eye (e.g., retinopathies, age related macular degeneration, diabetic macular degeneration, and choroidal melanoma).

Drusen are hyaline deposits in Bruch's membrane beneath the retina. The deposits are caused by, or are at least markers of inflammatory processes. They are present in a large percentage of patients over the age of 70. Although causality is not known, drusen are associated with markers of the location where inflammation is occurring and where neovascularization has a high likelihood of occurring in the future; these are regions of so called "vulnerable retina." Therefore, applying inflammation reducing radiation to the region may be beneficial to the patient.

Radiation therapy has historically been marginally successful in treating disorders of the eye; for example, in a recent Cochrane meta-analysis review (Cochrane Database 2007 (2), the entirety of which is incorporated herein by reference), the authors discussed the merits of radiation therapy for AMD. Among their general conclusions was as follows: ophthalmologists were reluctant to refer patients to the radiation oncologists for fear that they would lose their patients; it was difficult to localize the radiation source because specific methods were not used for the clinical protocol; and fractionation schemes and dosing was not standardized. Therefore, there is a great need for the systems and methods described in this disclosure.

Brachytherapy described above appears to have a highly beneficial effect at least when combined with pharmaceutical therapy as an adjuvant therapy. Brachytherapy definitively localizes the radiation dose to the region to be treated and ensures that the dose is delivered at a high rate. However, brachytherapy is difficult to control as far as a treatment plan (e.g., the surgeon can hold the probe in a variety of positions for any given patient) and the brachytherapy source typically cannot be turned off (e.g., strontium has a 29 year half-life).

Radiotherapy System

The Portable Orthovoltage Radiotherapy Treatment system (PORT) 10 in FIG. 1A can be configured to deliver anywhere from about 1 Gy to about 40 Gy or from about 10 Gy to about 20 Gy to regions of the eye including the retina, sclera, macula, optic nerve, the capsular bag of the crystalline or artificial lens, ciliary muscles, lens, cornea, canal of schlemm, choroid, conjunctiva, etc. In some embodiments, the system can be configured to deliver from about 15 Gy to about 25 Gy. In some embodiments, the system 10 is capable of delivering x-ray therapy in any fractionation scheme (e.g. 5 Gy per day or 10 Gy per month or 25 Gy per year) as the treatment planning system can recall which regions had been treated based on the unique patient anatomical and disease features. These features and previous treatments are stored in the treatment database for future reference.

The system can also deliver different photon energies depending on the degree of disease or the region of the eye being treated. For example, the x-ray generation tube can deliver from about 20 KeV photons to about 40 KeV photons or to about 60 KeV photons, or to about 100 KeV photons. It may be desirable to use about 20 KeV to about 50 KeV photons for structures in the anterior portion of the eye because these energies will penetrate less whereas it may be desirable to utilize from about 60 KeV to about 100 KeV photons or greater for structures in the posterior region of the eye for greater penetration to the retina. In some embodiments, the x-ray generation tube can deliver photons with photon energies from about 10 keV to about 500 keV, from about 25 keV to about 100 keV, from about 25 keV to about 150 keV, and/or from about 40 keV to about 100 keV. In some embodiments, selection of the photon energy can be based on diagnostic calculations, which can include a model of the eye created from anatomic data taken from the actual eye.

Although generally specific for the eye in this disclosure, PORT can be applied to any superficial body structure within reach of orthovoltage x-rays or to structures accessible during surgical procedures. For example, in regions such as the breast, it may be desirable to use x-rays with energies greater than about 40 keV but less than about 200 keV to reach the structures of interest. Other structures of interest include, for example, skin lesions, facial lesions, mucosal lesions of the head and neck, nails, muscles, soft tissues, anorectal regions, prostate, genital regions, joints, tendons, muscles, and the urogenital tract.

PORT can be applied to specific structures within the eye while sparing others because of its imaging systems, its modeling systems, and its finely-tunable collimators can provide precisely directed x-ray beams that can be targeted on specific structures within the eye with small penumbras (for example, 1-5 mm beams with less than 10% penumbra). PORT therapy is also based on individualized, biometric representations of the eye which allows a personalized treatment plan to be created for every patient.

As described above, orthovoltage generators, or other low energy x-ray generators, allow for the system to be placed in a room without requiring thick protective walls or other special shielding apparatus or special controls which would be prudent with devices generating x-rays with photon energies greater than about 500 keV. Orthovoltage generators, or other low energy x-ray generators, are also more compact than linear accelerators which allow them to be moved and directed with less energy from control motors as well as with less internal and external shielding. The lower energy x-ray generators also allow for simpler collimation and beam directing schemes with small penumbras and tight collimation. In addition, in a scheme where it is desired to move the x-ray source, much less energy is used to move the source to different positions, and the entire system is scaled down in size with lower energy x-ray sources.

In some embodiments, the radiotherapy system is used to treat a wide variety of medical conditions relating to the eye. For example, the system may be used alone or in combination with other treatments to treat macular degeneration, diabetic retinopathy, inflammatory retinopathies, infectious retinopathies, tumors in the eye or around the eye, glaucoma, refractive disorders, cataracts, post-surgical inflammation of any of the structures of the eye (e.g., trabeculoplasty, trabeculectomy, intraocular lenses, glaucoma drainage tubes, corneal transplants, infections, idiopathic inflammatory disorders, etc.), ptyrigium, dry eye, and other ocular diseases or other medical conditions relating to the eye.

The radiotherapy treatment system preferably includes a source, a system to control and move the source, an imaging system, and an interface for a health care professional to input treatment parameters. Specifically, some embodiments of the radiotherapy system include a radiotherapy generation module or subsystem that includes the radiation source and the power supplies to operate the source, an electromotive control module or subsystem which operates to control the power to the source as well as the directionality of the source, a coupling module which links the source and control to the structures of interest (e.g., the eye), and an imaging subsystem; these modules are linked to an interface for a healthcare professional and form the underpinnings of the treatment planning system. The terms "module" and "subsystems" can be used interchangeably in this disclosure.

FIG. 1A illustrates a side view of embodiments of a system 10 for treating ocular diseases using radiotherapy. In the embodiments illustrated, the radiotherapy treatment system 10 comprises a radiotherapy generation module or subsystem 110, a radiotherapy control module or subsystem 120, an interface display 130, a processing module 140, a power supply 150, a head restraint 160, and an imaging module with a camera 400.

In some embodiments, the radiotherapy device delivers x-rays to the eye 210 of a patient 220. The power supply 150 preferably resides inside the system 10 or adjacent the system 10 (e.g., on the floor). In some embodiments, however, the power supply 150 can reside in a different location positioned away from the system 10. The power supply 150 can be physically coupled to the x-ray generator 110 (in a monoblock configuration) or can be uncoupled from the x-ray generator (e.g., the x-ray source moves independently of the power supply and is connected through high power cables). In some embodiments, a cooling system for the X-ray tube is also provided. The cooling system can be water or oil or air convection and can be attached or located a distance from the radiotherapy system 10.

Voltage can be wall voltage of about 110V or 220V (with assistance of a transformer) which can be used for the devices in the system shown in FIG. 1A. Currents to drive x-rays out of the device may be on the order of 1 amp or lower down to about 50 mA or even about 5-10 mA. What is desired of the power supply is that a high voltage be generated to drive the electrons from the cathode in the x-ray tube to the anode of the x-ray; electron movement is performed within a vacuum inside the x-ray tube. The high voltage (e.g., about 30,000-300,000 volts or higher) may be desired to accelerate the electrons inside the vacuum. A second current is typically used with x-ray power supplies in order to generate the electrons from a filament, the electrons are subsequently accelerated through the voltage potential. Therefore, x-ray power supplies typically have two power supplies in order to generate x-rays. Once generated, the electrons speed toward the anode under the influence of the high voltage potential; the anode is where the x-ray generating material typically rests (e.g., tungsten, molybdenum).

Once the electrons strike the x-ray generating material target, x-rays are generated. An absorbing metal (e.g., aluminum, lead, or tungsten) within the casing of the system of FIG. 1A will absorb much of the generated x-rays which have been scattered from the source 110. The x-rays, which are pre-planned to escape, are emitted from the source and travel into a collimator (e.g., a primary or secondary collimator) and optionally through a filter (e.g. an aluminum filter). The collimator is intended to direct the x-rays toward the patient 220. Notably, as described herein, collimators can be designed and manufactured so as to minimize penumbra formation and scatter and to optimize the shape and/or direction of the x-ray beam. The power supply is preferably connected to the x-ray source by a high power cable that is highly insulated to prevent power leakage.

The collimator can be one or more collimators (e.g., a primary 1030 and a secondary collimator 1040, and even a third collimator 1052, as illustrated in FIG. 2A). In some embodiments, a secondary (shaping) collimator is placed close to the eye 1300 (e.g., within 10 cm) of the patient, and the primary collimator 1030 is placed close to the source 1070. This type of configuration can decrease the penumbra generated by the source 1070 on the ocular structures 1300.

In some embodiments, collimators are specialized apertures. The apertures can be adjustable; for example, the aperture can be adjustable from about 1.0 cm to about 0.5 mm or below 0.5 cm to about 0.01 cm. In some embodiments, the aperture is adjustable (e.g., automatically or manually by the operator of the machine) between about 0.5 mm and about 7.0 mm. In some embodiments, the collimator is constructed from tungsten, lead, aluminum, or another heavy metal. In some embodiments, the collimator has a cylindrical shape for the radiation to pass through; in other embodiments, the collimator has a coned shape for the radiation to pass through. In some embodiments, the collimator aperture has a rounded shape. In certain embodiments, the collimator has a curvilinear shape for the x-ray to pass through. In some embodiments, the collimator is cut using wire-EDM; in other embodiments, the collimator path is cut and polished using a laser. The smooth contour of the collimator allows for minimal scattering as the radiation passes through the collimation apparatus. In some embodiments, the collimator has a region of thinner metal than another region so that the beam is relatively modified but does not have a sharp contour.

In some embodiments (FIG. 2C), a light pointer 1410 (e.g., a laser beam emitted from a source 1450) is coupled to a collimator 1405, or behind the collimator 1405, so that the light pointer 1410 is coincident with an x-ray beam 1400; the light pointer 1410 can indicate the position on a surface of an eye 1300 through which the radiation source enters by tracking angles of incidence 1420, 1430 of the collimator and x-ray beam. The collimator 1405 is preferably co-linear with the light source 1450 which can act as a pointer to indicate the point on the eye through which the radiation enters the eye 1300.

In some embodiments, a laser pointer 1210, illustrated in FIG. 2B' sits on top of, or is coincident with the x-ray beam through the primary or secondary collimator 1215. The laser pointer 1210 can be reflected off a reflector 1220 that aligns the laser pointer 1210 with the collimator opening 1216 such that the laser point 1210 strikes substantially the same position of a surface beyond the collimator opening as does the x-ray 1200. The reflector 1220 can be a beam splitter, and the beam splitter can be transparent to x-ray energy 1200. The laser pointer 1210 can emit a wavelength that is detectable by the system camera 1460. Because the pointer is seen on the camera, the pointer indicates where the radiation beam enters the eye. The pointer 1410 can also serve as a visual verification that the x-ray source is powered on and directed in the proper orientation with respect to the ocular structure, or target tissue 1480, of interest. With a second camera in the system, the angle of incidence of the laser pointer and the x-ray beam can be determined.

At least one camera 400, 1460 is included in the system to at least track the eye in real time. In some embodiments, the camera 400, 1460 images the eye with or without the x-ray source tracking device (e.g., laser pointer) described above. The camera can detect the position of the eye and relate the direction of the x-ray and collimator system to the position of the eye. An optional display 130 directed to the operator of the radiotherapy system on the system 10 can depict the position of the x-ray device in real time in some embodiments.

In another embodiment (FIG. 4), the camera 2055 detects the position of the eye and digitizing software is used to track the position of the eye. The eye is meant to remain within a preset position 2060; when the eye deviates from the position 2060 beyond a movement threshold, a signal 2090 can be sent to the radiation source 2000. As used herein, the term "movement threshold" is intended to have its ordinary meaning, which includes, without limitation, a degree or measurement that the eye is able to move and still be within the parameters of treatment without shutting the radiation source 2000 off. In some embodiments, the movement threshold can be measured in radians, degrees, millimeters, inches, etc. The radiation source 2000 is turned off when the eye is out of position 2057 beyond the movement threshold, and the radiation source is turned on when the eye is in position 2054, or within the movement threshold.

Figure 1B:
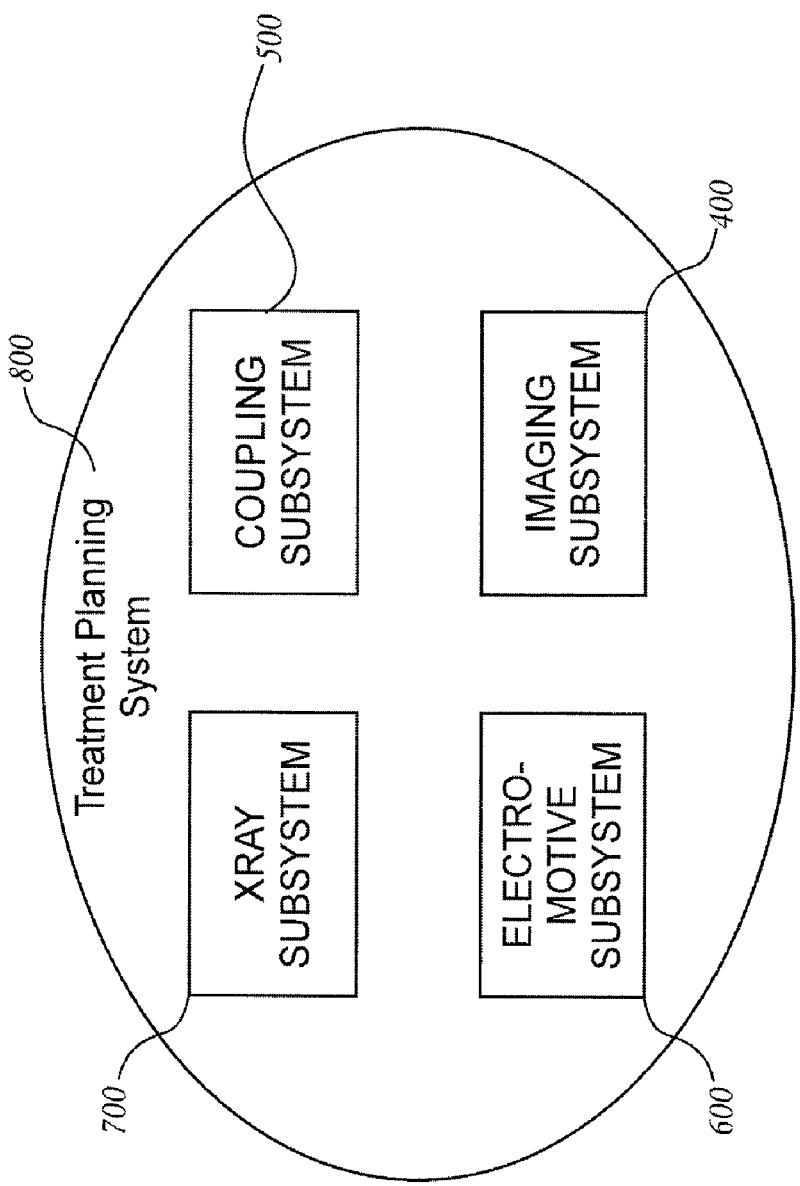
FIG. 1B is a schematic format of embodiments of a radiotherapy treatment system.
Figure 1C:
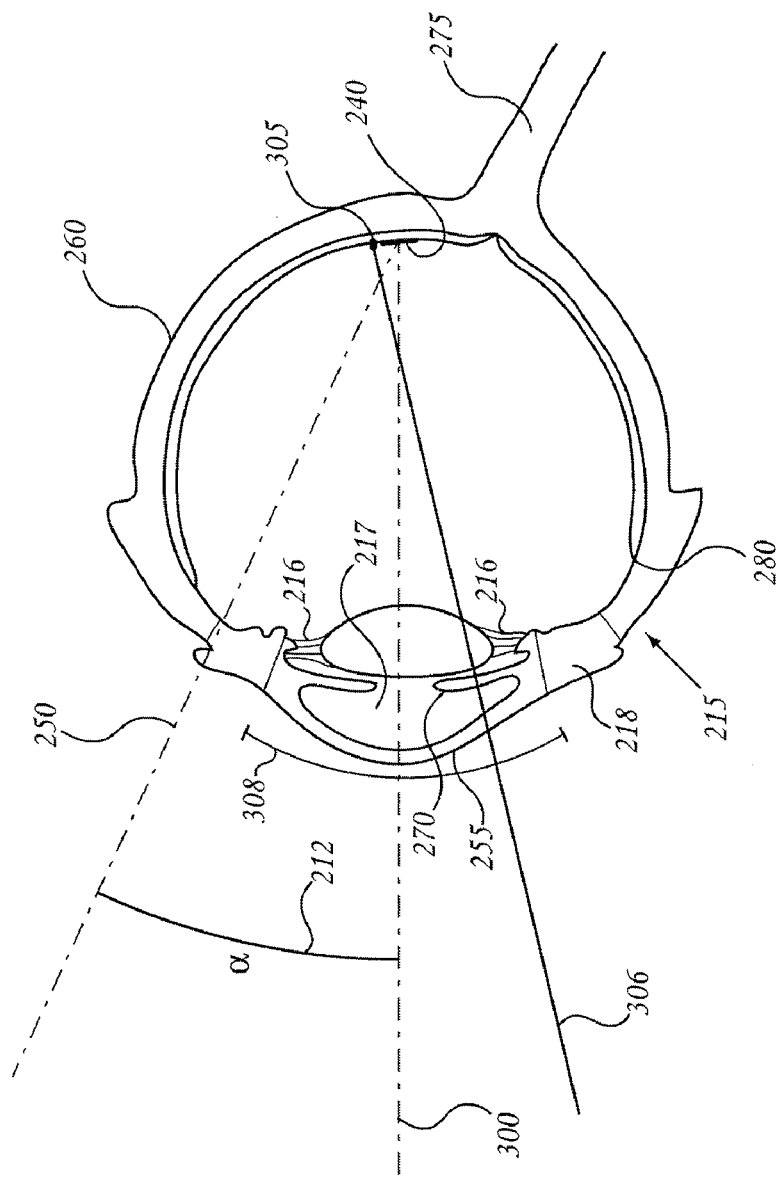
FIG. 1C is a schematic of the eye.
Figure 1D:
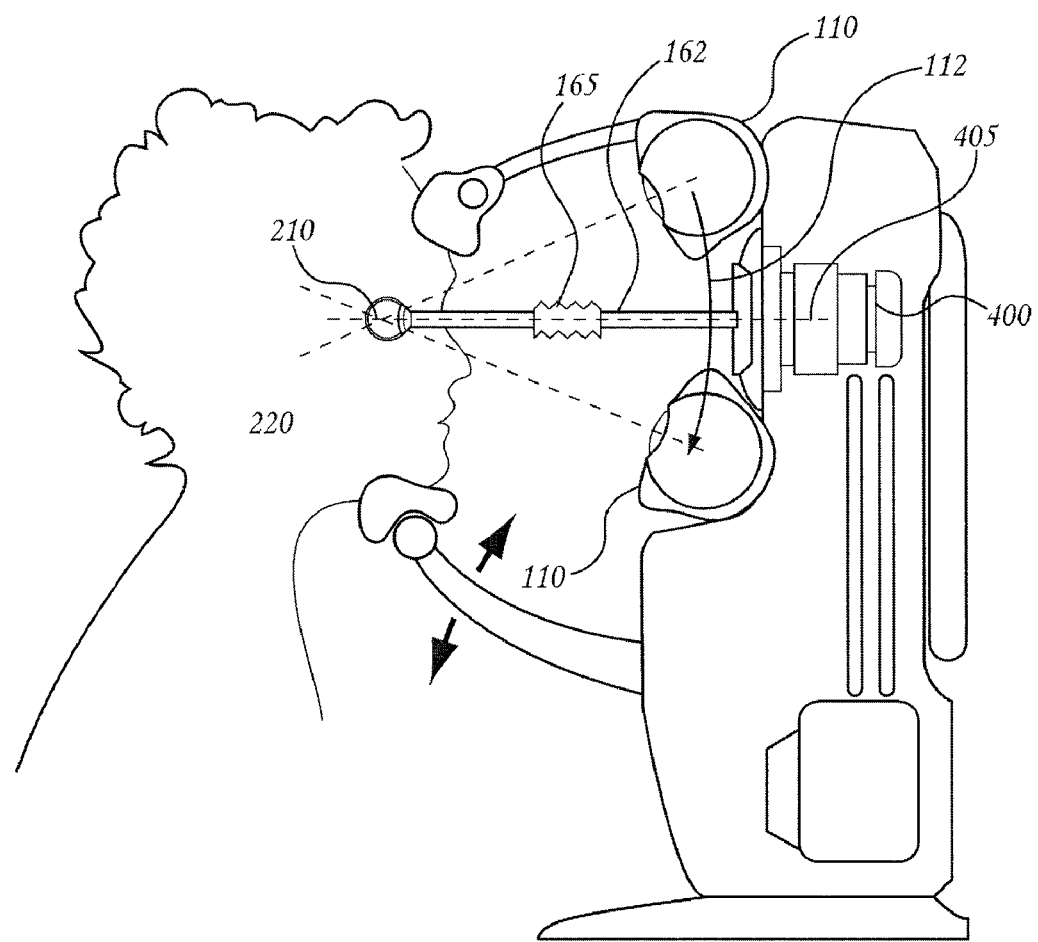
FIGS. 1D and 1E depict embodiments of a radiotherapy system which communicates with a lens on the eye.
Figure 1E:
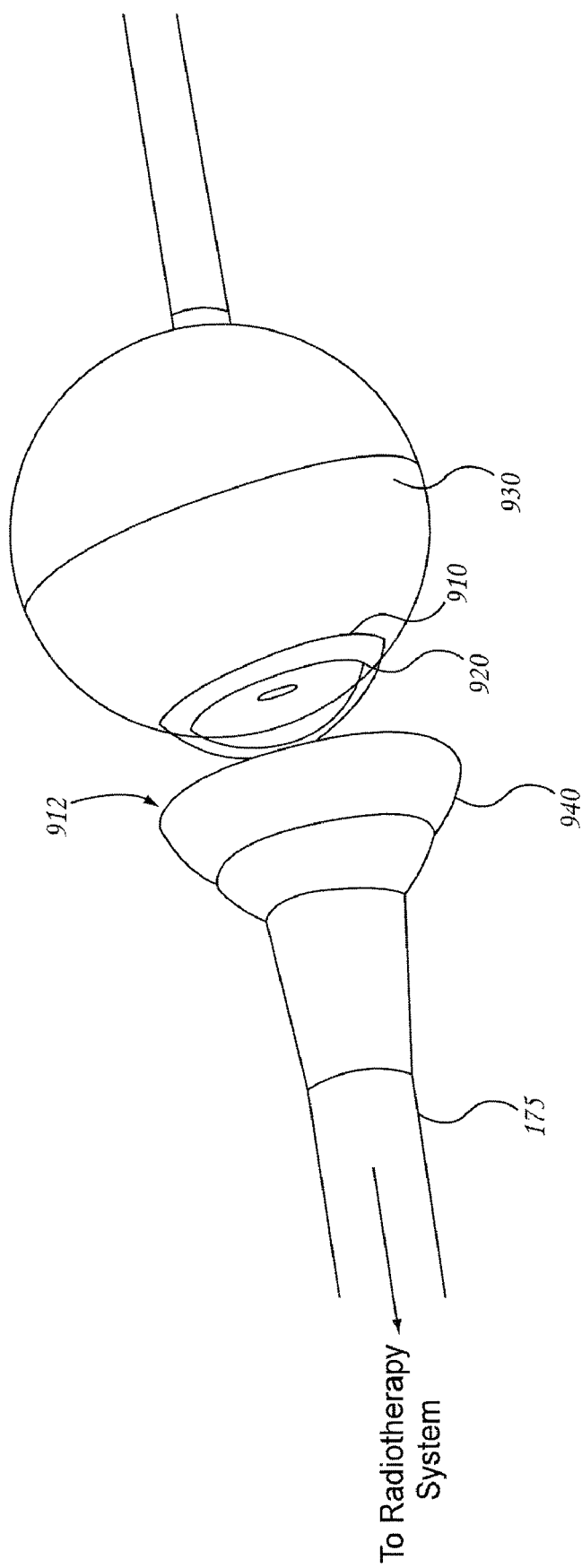

In some embodiments, a connection, or coupling, 162 extends from the system and contacts the eye 210 (FIGS. 1D-1E). The connection can be a physical connection which can include an optical or other communication between the system and the eye in addition to a mechanical connection. The physical connection 162 can serve several functions. For example, in some embodiments, the connection 162 is a mechanical extension which allows the position of the eye to be determined because it is directly applied to the cornea or sclera. It also provides for inhibition of the eye so that the patient is more inclined to be compliant with keeping their eye in one position throughout the treatment. In addition, the eye can be moved into a pre-determined position, in the case, for example, when the patient's eye has been paralyzed to perform the procedure. Finally, the physical contact with the eye can be used to protect the corneal region using an ophthalmic lubricant underneath the physical contact device. The physical connection 162 from the cornea allows for positioning of the eye with respect to the system.

The physical connection 162 to the eye from the radiotherapy system 10 can contact the limbus 910 (also see FIG. 1C 308) around the eye or can contact the cornea 920 or the sclera 930. The physical connection can contain a suction type device 912 which applies some friction to the eye in order to move the eye or hold the eye in place with some force. In certain embodiments, the connection 162 contacts the sclera when suction is applied. The physical connection 162 can dock onto a scleral lens 940 or a corneal lens which is inserted separately into or onto the eye; piece 160 then docks into or onto the scleral or corneal contact lens. Any of the materials of the physical connection can be transparent to x-rays or can absorb some degree of x-ray. The physical connection 162 can help to stabilize the eye of the patient, preventing eye movement underneath the lens. If a lubricant is inserted inside the lens, the lens can hold a gel or lubricant to protect the eye during the procedure. The lens can also contain through holes which can provide the cornea with oxygen.

The physical connection 162 can be movable with respect to the remainder of the radiotherapy system; the physical connection 162 can be rigid, substantially rigid, or can contain a spring 165, which allows flexibility in the axial or torsional direction. In some embodiments, the connection 162 is not mechanical at all but is an optical or other non-contact method of communicating between a radiotherapy system and a lens 940 positioned on the eye. The physical connection 162 can signify the coordinate reference frame for the radiotherapy system and/or can signal the movement of the device with respect to the eye. Connection 162 can therefore assist in maintaining eye location in addition to maintaining eye position by inhibiting movement of the patient. Physical connection 162 can contain radiotransmitters or features which can be captured on a camera so that the eye can be located in three-dimensional space.

In some embodiments, the physical connection 162 to the eye is docked into position on the eye by the physician so that it identifies the center of the limbus and the treatment axis through its center. The position of the eye can then be identified and tracked using by the radiotherapy system. With knowledge of the center of the limbus in combination with the eye model, the radiotherapy system can then be directed about the treatment axis and center of the limbus to deliver radiation to the retina.

X-ray source 110 can travel around a central axis 405 or a focal point within the eye 210, such as, for example, illustrated in FIG. 1D by arrows 112. Alternatively, the x-ray source 110 can travel around a floating focal point as defined by the treatment planning system and virtual model of the eye. A floating focal point is one anywhere in the eye as opposed to a fixed focal point such as the macula for example. In some embodiments, the x-ray source can move with six degrees of freedom around a fixed or moving axis. In some embodiments, the x-ray source remains fixed in one spot to treat an eye structure in the anterior portion of the eye or even the posterior portion of the eye depending on how large an area is to be treated and the dose required. In some embodiments, the x-ray source 110 focuses x-rays on a target by moving to different positions around the eye and delivering x-rays through the sclera at substantially different entry points on the sclera but each x-ray beam reaching a substantially similar target within the eye. In some embodiments, the x-ray source remains in one location, delivering x-ray energy to and through the sclera and to regions within the eye, such as the retina and specifically the macula. In some embodiments, the x-ray source 110 is moved with five degrees of freedom, four degrees of freedom, three degrees of freedom, or two degrees of freedom. In some embodiments, the x-ray source 110 is stationary and the collimator is moved or the eye or the patient is moved to project the beam to different regions of the eye. In some embodiments, the retina is treated by maintaining the x-ray beam in one position with respect to the sclera. The x-ray source 110 can be moved automatically by a robotic arm or manually by the operator of the system. The ultimate three-dimensional position of the x-ray source 110 can be dictated by the treatment plan which communicates between a model of the eye and with the robotic arm to determine the position of the x-ray beam relative to the eye.

In some embodiments, only a small amount of movement is required of the x-ray source to entirely treat a disease of the retina, such as macular degeneration and/or diabetic macular edema. In these embodiments, six degrees of freedom can be applied to the x-ray source 110, but the range of each degree of freedom is preferably limited so that the movement system only travels within a volume of about 1000 cm$^3$, 500 cm$^3$, 100 cm$^3$, or about 50 cm$^3$. The speed of the robot within these volumes can be defined such that the robot moves 0.5 cm/s, 1 cm/s, 3 cm/s, 5 cm/s. Because each fractional treatment dose is relatively short and applied over a small distance, the robot can sacrifice speed and travel distance for smaller size.

In some embodiments, it is a goal of the treatment system to deliver radiation therapy substantially through the pars plana region of the eye (see FIG. 1C). Pars plana 215 is the region of the eye between the pars plicata 218 and a peripheral portion of the retina 280, the ora serrata. The pars plana 215 region of the eye contains the fewest critical structures enroute from the sclera 260 to the retina 280. It is typically the region through which surgeons will inject pharmaceuticals in order to inject drugs into the eye or to perform vitrectomies because the smallest risk of damage to ocular structures exists with this approach. Likewise, radiotherapy can be delivered to the posterior region of the eye through the pars plana region 215 to minimize the potential for damage to structures such as the lens, yet reaching regions such as the fovea 240 and with minimal radiation reaching the optic nerve 275. The image-guided orthovoltage therapy described herein allows such specific treatment.

The central axis 300 of the eye is typically defined by the geometric axis 300, but in some embodiments, it can be defined by the visual axis 305; the visual axis of the eye is represented by a line 306 from the center of the fovea 305 through the center of the pupil. The geometric axis 300 can be defined by a perpendicular straight line 300 from the center of the limbus 308 straight directly back to the retina; this axis can also be referred to as the treatment axis. The limbus 308 is technically the point where the cornea meets the sclera or visually the point where the pigmented region of the eye meets the white region of the eye. The pars plana angle 212 can be measured from the geometric central axis 300 and can range from about 10 degrees to about 50 degrees off the central geometric axis 300. The visual axis 306 is the straight line from the center of the macula 240 and out the front of the eye through the center of the pupil 217. The pars plana 215 region of the eye can be related to the central axis 300 of the eye through an angle α 212. In some embodiments, x-rays with a tight collimation (e.g., smaller than about 6-8 mm in diameter) and a small penumbra (e.g., less than about ten percent at the sclera) enter the pars plana region 215 of the eye, avoiding some of the critical structures of the eye, to reach structures which are to be treated, such as the retina. In some embodiments, during the treatment, the eye can be stabilized with the assistance of physical or mechanical restraint or by patient fixation on a point so that the x-rays enter the eye substantially only in the pars plana region 215.

In certain embodiments, the patient is stabilized with respect to the axis of the eye. If the patient or device moves, then the camera detects the movement and turns the device off or closes a shutter over the region the x-rays leave the device or the collimator. In some embodiments, the x-ray source 110 is moved about the eye to one or more positions determined by a treatment planning system, delivering radiation through the pars plana region 215 of the eye to reach the retina. The total dose is divided across different regions of the sclera but penetrates through the pars plana 215 region to reach the desired region of the retina (for example, the macula or the fovea).

The head restraint 160 portion of the radiotherapy system 10 may be used for restraining the head of the patient 220 so as to substantially stabilize the location of the patient's eye 210 relative to the radiotherapy treatment system 10. The physician applying the treatment can align the central axis 300 of the patient's eye with the x-ray source. The restraint 160 can maintain the patient's position during the treatment. If the patient moves away from the restraint 160 or moves their eyes from the restraint, then the x-ray machine can be turned off (gating) manually or automatically and the patient's position readjusted.

In general terms, the patient's head is maintained in position with the head restraint 160 while the eye 210 is tracked by the imaging system 400 and/or treatment planning system and the x-ray source 110 is moved so that the x-ray beam enters the eye through the pars plana region 215; the x-rays, therefore, penetrate to the target regions of the retina and create minimal damage on their way to the retina.

The treatment planning system 800 (FIGS. 1B and 2E) provides the physician interface with the system 10. The treatment plan is developed based on pre-treatment planning using a combination of biometric modalities including an imaging subsystem that can include, for example, OCT, or optical coherence tomography, CT scans, MRI scans, and/or ultrasound modalities. The information from these modalities are integrated into a computer-generated virtual model of the eye which includes the patient's individual anatomic parameters (biometry) as well as the individual's specific disease burden. The treatment plan is output, for example, on the interface display 130 module of the radiotherapy system 10. The physician can then use the virtual model in the treatment plan to direct the radiation therapy to the disease using the radiotherapy system 10.

As used herein, "eye model" or "model of the eye" refers to any representation of an eye based on data, such as, without limitation, an anteroposterior dimension, a lateral dimension, a translimbal distance, the limbal-limbal distance, the distance from the cornea to the lens, the distance from the cornea to the retina, a viscosity of certain eye structures, a thickness of a sclera, a thickness of a cornea, a thickness of a lens, the position of the optic nerve relative to the treatment axis, the visual axis, the macula, the fovea, a neovascular membrane, and/or an optic nerve dimension. Such data can be acquired through, for example, imaging techniques, such as ultrasound, scanning laser ophthalmoscopy, optical coherence tomography, other optical imaging, imaging with a phosphor, imaging in combination with a laser pointer for scale, and/or T2, T1, or functional magnetic resonance imaging. Such data can also be acquired through keratometry, refractive measurements, retinal nerve-fiber layer measurements, corneal topography, etc. The data used to produce an eye model may be processed and/or displayed using a computer. As used herein, the term "modeling" includes, without limitation, creating a model.

FIG. 1B depicts a schematic overview of the x-ray treatment system 10. For conceptual simplicity, the components of the system are depicted in the four boxes. The overall treatment planning system 800 is depicted by the background oval shape, depicting a global interconnect between the subsystems. The treatment planning system 800 directs the four subsystems toward treatment of the region indicated by the physician. The four subsystems in general terms include an x-ray subsystem 700, a coupling subsystem 500, an electromotive subsystem 600, and an imaging subsystem 400. These subsystems or modules interact to provide an integrated treatment to the eye of a patient.

The subsystems work together to coordinate the treatment planning system 800. The treatment planning system (TPS) 800 also provides the interface between the physical world of the eye, the physical components of the system, and a virtual computer environment which interacts with the physician and treatment team and contains the specific patient and disease information. The coupling system 500, primarily, and the imaging system 400, secondarily, help link the physical world and the virtual world.

The virtual world contains a computer-generated virtual model of the patient's eye 505 based on physical and biometric measurements taken by a health practitioner or the imaging system 400 itself. The computer model 505 (FIG. 2D) in the virtual world further has the ability to simulate the projection 510 of an x-ray beam 520 from a radiation source 524 through an anterior region of the eye 515 to the structure 514 to be treated on or in the eye 514 based on different angles of entry into the eye. The model can also include important eye structures, such as the optic nerve 512, to consider during the treatment planning process. The virtual world also contains the physician interface to control the device 524 and interface the device with respect to the physical world, or that of the actual physically targeted structure. After integrating the inputs from the physician and modeling the beam angles and desired direction to direct the therapy, the virtual world outputs the information to the electromotive subsystem to move the x-ray device to the appropriate position in three-dimensional space. The coupling subsystem 500 (in the physical world) can include a mechanism to determine the angle of incidence of the x-ray beam with respect to the surface of the eye using one or more laser or angle detectors, as discussed above.

In some embodiments, the coupling system 500 contains a camera 518 which can image a spot 516 on or in an eye. Information from the camera is then preferably transferred to the virtual eye model 522 and again to the motion and radiotherapy system 524. In certain embodiments, the coupling system 500 is a physical connection with the eye. In some embodiments, the coupling system 500 is not a physical link but is a communication link between a lens on the eye and a detection system. For example, a lens can be a communication beacon to relay eye position to the system 500. In some embodiments, the lens can contain markers that are imaged by the imaging camera 518, through which the next stage in the therapy can be determined. In some embodiments, a combination of these techniques is used.

In some embodiments, the position of the eye and the x-ray source are known at all times, and the angles of entry of the x-ray can therefore be realized. For example, the central axis of the eye can be determined and the x-ray source offset a known angle from the central axis. The central axis, or treatment axis, in some embodiments can be assumed to be the axis which is perpendicular to the center of the cornea or limbus and extends directly posterior to the retina, as discussed previously. Alternatively, the coupling subsystem can detect the "glint" or reflection from the cornea. The relationship between the glint and the center of the pupil is constant if the patient or the patient's eye is not moving. If the patient moves, then the glint relative to the center of the pupil is not in the same place. A detector can detect when this occurs, and a signal can be sent from the virtual world to the x-ray device to turn the x-ray device off or to shutter the system off.

The actual acquisition method notwithstanding, the information obtained from the coupling subsystem is preferably sent to the computer system and to the virtual eye model. The imaging subsystem 400 captures an image of the eye in real time with a camera 1460 and feeds the data into the software program that creates a virtual model of the eye. In combination with the physical world coupling system 500, the predicted path of the x-ray beam through the eye can be created on the virtual image. Depending on the region to be treated, the electromotive system and/or x-ray system can be readjusted; for example, a robot arm can move the x-ray source 110 to a position to send a radiation or x-ray beam to a location on or in the eye based on the model of the eye as created by the TPS and as captured by the imaging system 400.

In certain embodiments, the radiotherapy generation system 100 can include an orthovoltage (or low energy) radiotherapy generator as the x-ray subsystem 700, as discussed in further detail with reference to FIG. 1A, a schematic of the device. The radiotherapy generation subsystem 110 generates radiotherapy beams that are directed toward the eye 210 of the patient 220 in FIG. 1A. In certain embodiments, the radiotherapy control module 120 includes an emitter 200 that emits a directed, narrow radiotherapy beam generated by the radiotherapy generation subsystem 110. As used herein, the term "emitter" is intended to have its plain and ordinary meaning, and the emitter can include various structures, which can include, without limitation, a collimator. In some embodiments, the control module 120 is configured to collimate the x-ray beams as they are emitted from the radiotherapy generation subsystem 110. The x-ray subsystem 700 can direct and/or filter radiotherapy rays emitted by the x-ray tube so that only those x-rays above a specific energy pass through the filter. In certain embodiments, the x-ray subsystem 700 can include a collimator through which the pattern or shape of an x-ray beam is determined. The filtering of the source preferably determines the amount of low energy inside the x-ray beams as well as the surface-depth dose as described in ensuing figures. In some embodiments, it is desirable to deliver orthovoltage x-rays with a surface-to-depth dose less than about 4:1 to limit dose accumulation at the surface of the eye. In some embodiments, it is desirable to have a surface-to-depth dose less than about 3:1 or 1.5:1 but greater than about 1:1 when using orthovoltage x-rays. Therefore, the radiotherapy control system can control one or more of the power output of the x-ray, the spectrum of the x-ray, the size of the beam of the x-ray, and the penumbra of the x-ray beam.

In certain embodiments, the electromotive subsystem 600 of the radiotherapy system may move the x-ray source and the collimator to direct a narrow radiotherapy beam emitted from the x-ray source to irradiate specific regions of the patient's eye 210 by directing energy onto or into targeted portions of the eye 210, while at the same time avoiding irradiation of other portions of the eye 210. For example, the system 10 may target a structure of the posterior region of the eye, such as the retina, or a structure on the anterior region of the eye, such as the trabecular meshwork, the sclera, the cornea, the ciliary processes, the lens, the lens capsule, or the canal of schlemm. The system 10 can deliver radiotherapy to any region of the eye, including, but not limited to, the retina, the sclera, the macula, the optic nerve, the ciliary bodies, the lens, the cornea, Schlemm's canal, the choroids, the capsular bag of the lens, and the conjunctiva.

In certain embodiments, the x-ray subsystem 700 can collimate the x-ray to produce a narrow beam of specified diameter and shape. For example, in certain embodiments using a collimator, the diameter of the collimator outlet may be increased or decreased to adjust the diameter of the radiotherapy beam emitted by the collimator. In certain embodiments, the x-ray subsystem 700 can emit a beam with a diameter of about 0.1 mm to about 6 mm. In certain embodiments, the x-ray subsystem 700 can emit a beam with a diameter of less than about 0.1 mm. In certain embodiments, the x-ray subsystem 700 can emit a beam with a diameter of between about 0.5 mm and about 5 mm. As described in further detail below, narrow beams and virtual models are useful to ensure that the energy is applied to a specific area of the eye and not to other areas of the eye. In some embodiments (FIG. 2B'-2B'''), the radiation control module can emit an x-ray beam with a circular 1212 or non-circular 1214 shape; in some embodiments, the radiation control module can emit an x-ray beam with a rectangular shape 1214 or a square shape. In some embodiments, the radiation control module can emit an x-ray beam with an arc shape or an elliptical shape or a doughnut configuration 1217 through a circular collimator 1215 with an opaque region 1218 in the center. In some embodiment, the collimator 1215 can include a conical-shaped opening 1232, such as depicted in FIG. 2B'''', for providing a precisely shaped beam 1200.

In certain embodiments, the radiotherapy system 10 allows for selective irradiation of certain regions of the eye without subjecting other areas of the eye to radiation by using a narrow, directed treatment beam, the treatment beam dictated by the specific anatomy of the patient's eye. For example, the radiotherapy control module 120 can direct radiotherapy beams generated by the radiotherapy generation module 110 to a patient's macula, while substantially avoiding radiation exposure to other portions of the patient's eye, such as the lens, the trabecular apparatus, and the optic nerve. By selectively targeting specific regions of the eye with radiation based on knowledge of the anatomy of the eye and linking the radiation system to the anatomy for treatment purposes, areas outside of the treatment region may avoid potentially toxic exposure to radiation. In some embodiments, the x-ray beam follows a trajectory 250 that enters the eye through the pars plana region 215 which is a zone of the sclera 260 between the iris 270 and the retina 260. By directing the beam to this region and limiting the penumbra or scatter of the beam using specialized collimators, the beam can be localized onto an eye structure with minimal photon delivery to other structures of the eye, such as the cornea 255, the ciliary body and fibers 216 and other structures.

In certain embodiments, the radiotherapy treatment system 10 can include a shutter for controlling the emission of radiotherapy beams. The shutter may comprise a material opaque to the radiation generated by the radiation generation module 110. In certain embodiments, a shutter may be used to control the emission of beams from the radiotherapy generation module 110. In certain embodiments, a shutter may be used to control the emission of beams from the radiotherapy control module 120. In certain embodiments, the shutter may be internal to either of said modules 110 and 120, while in certain embodiments, the shutter may be external to either of said modules 110 and 120. In some embodiments, the system 10 is turned off to stop x-ray delivery, and in certain embodiments, the x-ray source 110 is turned off or its intensity turned down to limit or stop x-ray delivery to the target. In certain embodiments, the shutter or aperture changes shape or size.

In certain embodiments, and as explained above with respect to FIG. 1A, the radiotherapy treatment system 10 can deliver radiotherapy beams from one angle. In certain embodiments, the radiotherapy treatment system 10 can deliver radiotherapy beams from more than one angle to focus the beams on the treatment target. Certain embodiments of the system 10 that can deliver radiotherapy beams from more than one angle can include a plurality of stationary radiotherapy directing modules. The stationary radiotherapy modules can be positioned in a wide variety of locations to deliver radiotherapy beams to the eye at an appropriate angle. For example, certain embodiments of the radiotherapy treatment system 10 include five radiation source module-radiation directing module pairs that are connected to the radiotherapy treatment system 10 in such a way that they are spaced equidistantly around a circumference of an imaginary circle. In this embodiment, the power supply could be a switching power supply which alternates between the various x-ray generators. Certain embodiments of the system 10 that can deliver radiotherapy beams from more than one angle can include moving the radiotherapy directing module. Certain embodiments of the system 10 that can deliver radiotherapy beams from more than one angle can include moving the radiotherapy source using an electromotive subsystem 700 (FIG. 1B), such as a robot.

In some embodiments of the present disclosure, orthovoltage x-rays are generated from the x-ray generation module 700. X-ray photons in this orthovoltage regime are generally low energy photons such that little shielding or other protective mechanisms can be utilized for the system 10. For example, diagnostic x-rays machines emit photons with orthovoltage energies and require minimal shielding; typically, only a lead screen is used. Importantly, special rooms or "vaults" are not required when energies in the orthovoltage regime are used. Diagnostic x-ray machines are also portable, being transferable to different rooms or places in the clinical environment. In contrast, linear accelerators or LINACS which typically deliver x-rays with energies in the MeV range require thickened walls around the device because higher energy x-ray photons have high penetration ability. Concomitant with the higher energy photons, LINACS require much greater power and machinery to generate these high energy photons including high voltage power supplies, heat transfer methodologies, and internal shielding and protection mechanisms. This increased complexity not only leads to higher cost per high energy photon generated but leads to a much heavier device which is correspondingly more difficult to move. Importantly, as described above and demonstrated experimentally below, MeV photons are not necessary to treat superficial structures within the body and in fact have many disadvantages for superficial structures, such as penetration through the bone into the brain when only superficial radiation is required.

X-Ray Subsystem

The x-ray subsystem 700 generates x-rays and can include a power supply, a collimator, and an x-ray tube. In certain preferred embodiments, the x-ray subsystem 700 includes an orthovoltage x-ray generation system 1070 to produce orthovoltage x-rays with energies between 10 KeV and 500 KeV or even up to 800 KeV. This type of x-ray generation scheme is well known in the art and includes a high voltage power supply which accelerates electrons against a tungsten or other heavy metal target, the resulting collision then generating electromagnetic energy with x-ray energies.

Orthovoltage or low energy x-ray generators typically emit x-rays in the range from about 1 KeV to about 500 KeV or even up to about 1 MeV. In some embodiments, the system described herein emits x-rays with photon energies in the range from about 25 KeV to about 100 KeV. The use of low energy x-ray systems allow for placement of these x-ray treatment systems in outpatient centers or other centers and will not require the overhead and capital requirements that high energy (MeV or gamma) x-ray systems require. In the treatment of ophthalmologic disorders, such as AMD, placement in the ophthalmologist office or close to the ophthalmologic office is important because the ophthalmologists can treat many more patients, a very important component when treating a disease that afflicts millions of patients. If the device were limited to operating within vaults inside radiation oncology centers, the number of treatable patients would be much more limited because of access, cost, competition with other diseases, and other logistics.

The radiation generation module in some embodiments is composed of components that are arranged to generate x-rays. For example, a power supply generates current which is adapted to generate and accelerate electrons toward an anode, typically manufactured from a heavy metal such as tungsten, molybdenum, iron, copper, nickel, or lead. When the electrons hit one of these metals, x-rays are generated.

Figure 1F:
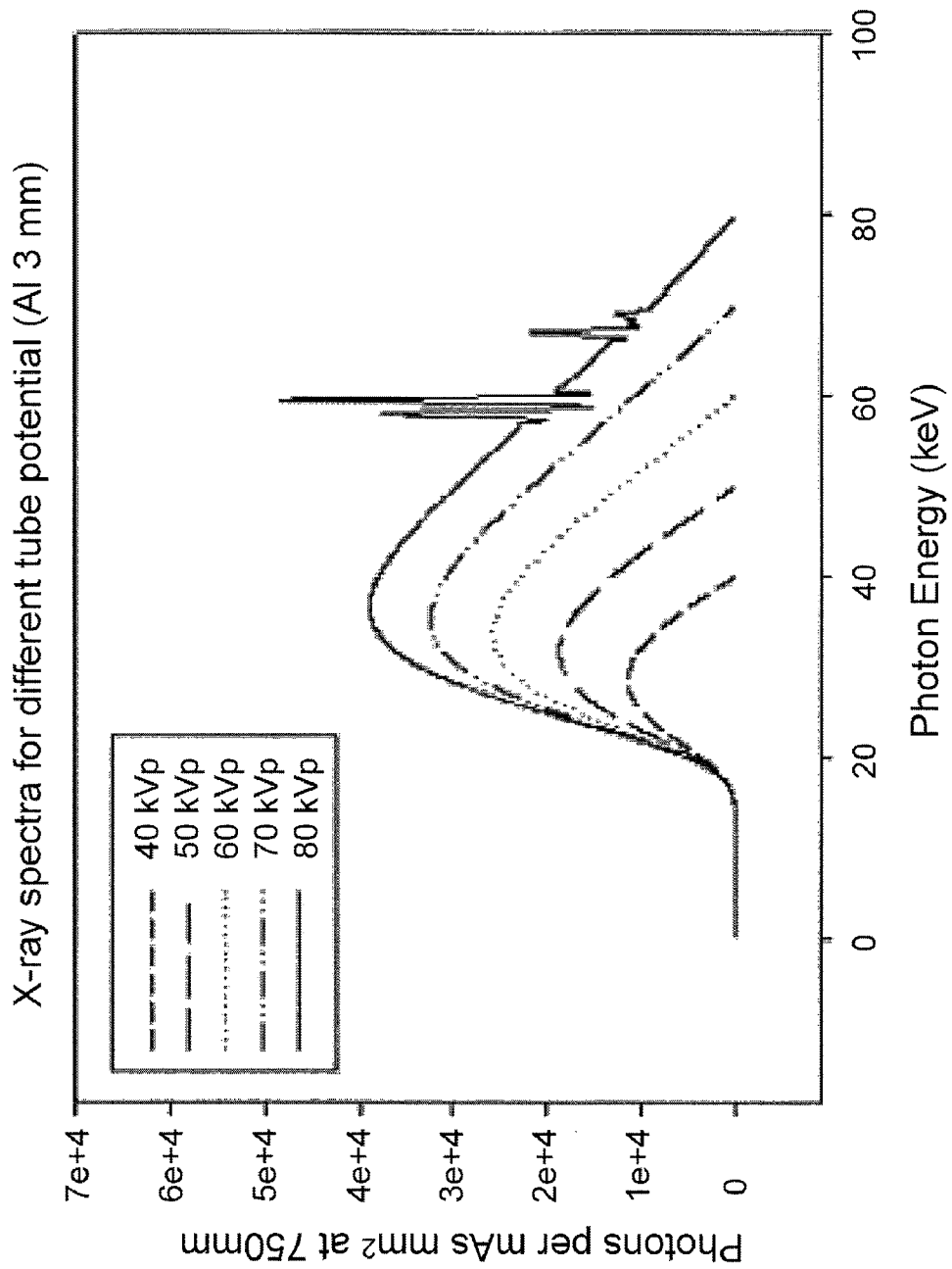
FIG. 1F depicts an x-ray radiation spectrum.

An exemplary set of x-ray spectra is shown in FIG. 1F. KVp refers to the maximum wavelength of the x-ray generated. For example, the 80 KVp spectra in FIG. 1F has a maximum of 80 KeV with a leftward tail of lower energy radiation. Similarly, the 60 KVp spectrum has a maximum of 60 KeV with a similar leftward tail. All spectra in the figure have been filtered through 3 mm of Aluminum for filtering which shapes the spectral curve as lower wavelengths are filtered to a greater degree than the higher wavelengths.

A power supply 150 as shown in FIG. 1A powers the radiation module. The power supply 150 is rated to deliver the required x-ray with a given current. For example, if 80 KeVp x-rays are being delivered from the source at 10 mA, then the power required is 800 W (80 kilovolts×0.01 A). Connecting the power supply to the x-ray source is a high voltage cable which protects and shields the environment from the high voltage. The cable is flexible and in some embodiments has the ability to be mobile with respect to the power supply. In some embodiments, the power supply is cooled with an oil or water jacket and/or convective cooling through fins or a fan. The cooling fluid can move through the device and be cooled via reservoir outside the system 10.

Electromotive Subsystem

FIG. 2A depicts embodiments of the electromotive subsystem 600 of the treatment system illustrated in FIG. 1B. The subsystem is an advantageous component of the therapeutic system because it controls the direction and the size of the x-ray beam. In general terms, the electromotive subsystem is directed in the space of the global coordinate system 1150 by the personalized eye model created from the patient's biometric data. The data from the model is transferred through the treatment planning system (TPS) to the electromotive subsystem 600 to direct the x-ray beam to the target on or in the eye.

In certain embodiments, the system can include a collimation system, a shutter system, and an electromechanical actuation system to move the x-ray source and/or collimators. Referring to FIG. 2A, orthovoltage x-ray source 1070 is depicted. Collimators 1030, 1040, and/or 1052 are calibrated to produce a small collimated beam 1062 of x-ray photons; in a preferred ophthalmic embodiment, the tightly collimated beam 1062 has an area of from about 1 mm$^2$ to about 20 mm$^2$ in a circular or other shape and a diameter of from about 0.5 mm to about 6.0 mm. Multiple collimators allow for improved penumbra percentages; the smaller the penumbra, the finer the application of x-rays to a specified structure. FIGS. 2B'-2B''' depicts embodiments of collimator designs in which a variety of collimator configurations are depicted. For example, FIG. 2B''' depicts a collimator configuration in which a doughnut shape of x-rays is generated; FIG. 2B'''' depicts a collimator configured with a nozzle, or conical, shape 1232 to limit the penumbra or create a substantially uniform radiation beam. The collimators, operating in conjunction with filters 1010, 1020 preferably cause the x-rays to leave the collimator in a beam 1090 having a substantially parallel configuration.

The electromotive subsystem 1100 interacts with and is under the direction of the global treatment planning system 800 in FIG. 1B. The electromotive subsystem 1100 receives commands from the treatment planning system 800 which can dictate among other things, the length of time the x-ray machine is turned on, the direction of the x-ray beam with respect to the eye target using data from the eye model or treatment planning system, the collimator size, and the treatment dose. The eye target 1300 and the control system 1100 can be linked in global coordinate space 1150 which is the basis of the coupling system. The treatment planning system 800 directs the therapy using global coordinate system 1150. The x-ray control system 1100 dictates the direction and position of the x-ray beam with respect to the ocular target and moves the x-ray source into the desired position as a result of commands from the treatment planning system 800.

In some embodiments, the collimators and/or the x-ray source can be placed on a moving wheel or shaft (1100, 1110, 1120) with one or more manual or automated degrees of freedom allowing the beam to be moved to a multitude of positions about the globe of the eye. In some embodiments, the x-ray source is movable with greater than one degree of freedom such as with a robot or automated positioning system. The robot moves the x-ray source with respect to a global coordinate system such as a cartesian coordinate system 1150 or a polar coordinate system. The origin of the coordinate system can be anywhere in physical space which is convenient. In some embodiments, the x-ray source is movable with four, five, or six degrees of freedom. In some embodiments, a robot is also utilized to move any of the other components of the x-ray control system such as the collimators. In some embodiments, the collimators are controlled with their own electromechanical system.

The electromotive subsystem can also contain one or more shutters to turn the beam on and/or off in an instant if desired (for example, if the patient were to move away). The x-ray source 1070 and/or collimators can move in any axis in space through an electromechanical actuation system (1100, 1110, 1120). In this embodiment, the treatment planning system can and then turning the device off when the eye is moved outside the target area.

Figure 2C:
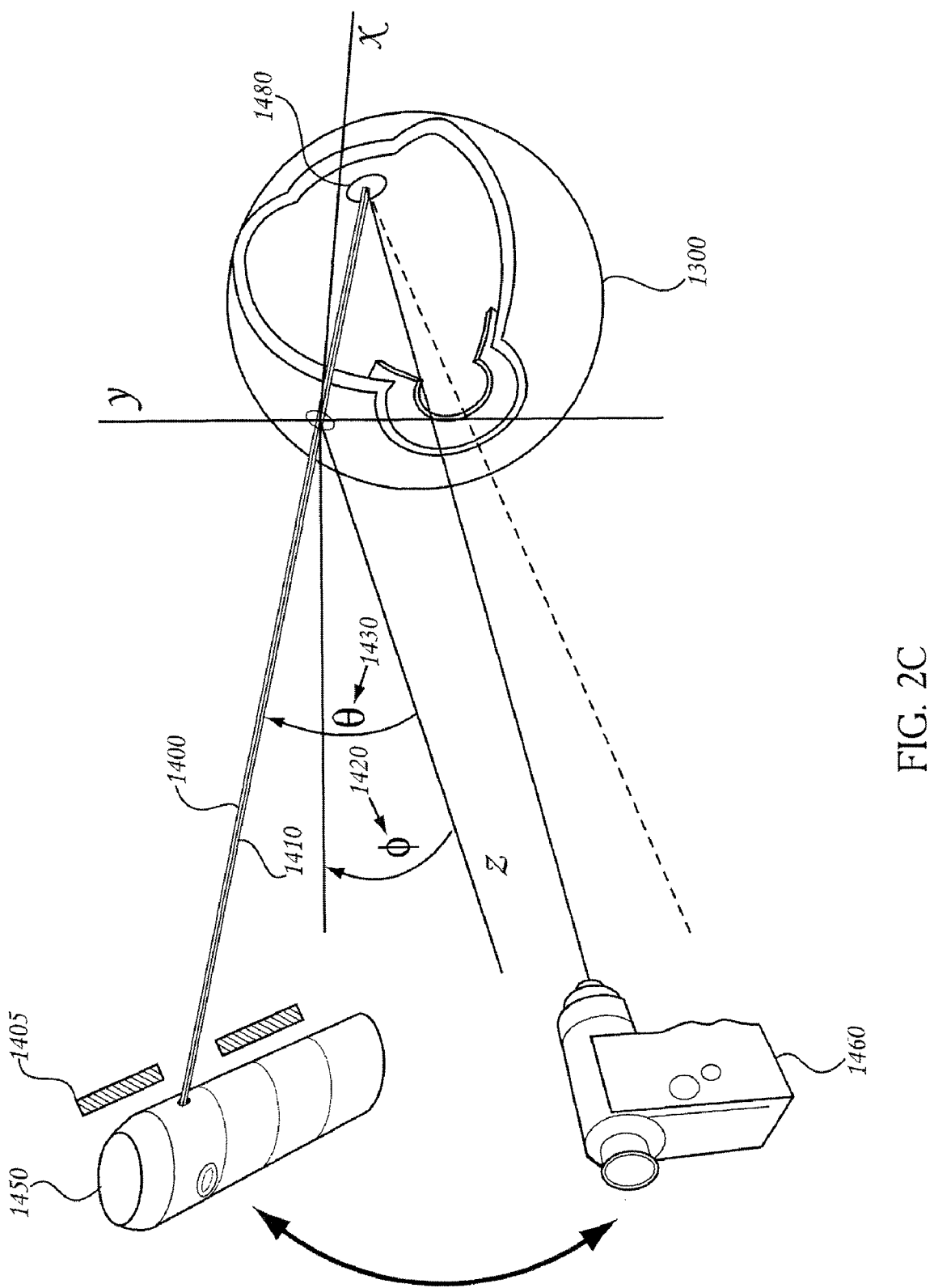
FIG. 2C illustrates embodiments of a radiotherapy system targeting a location within an eye for treatment.
Figure 2D:
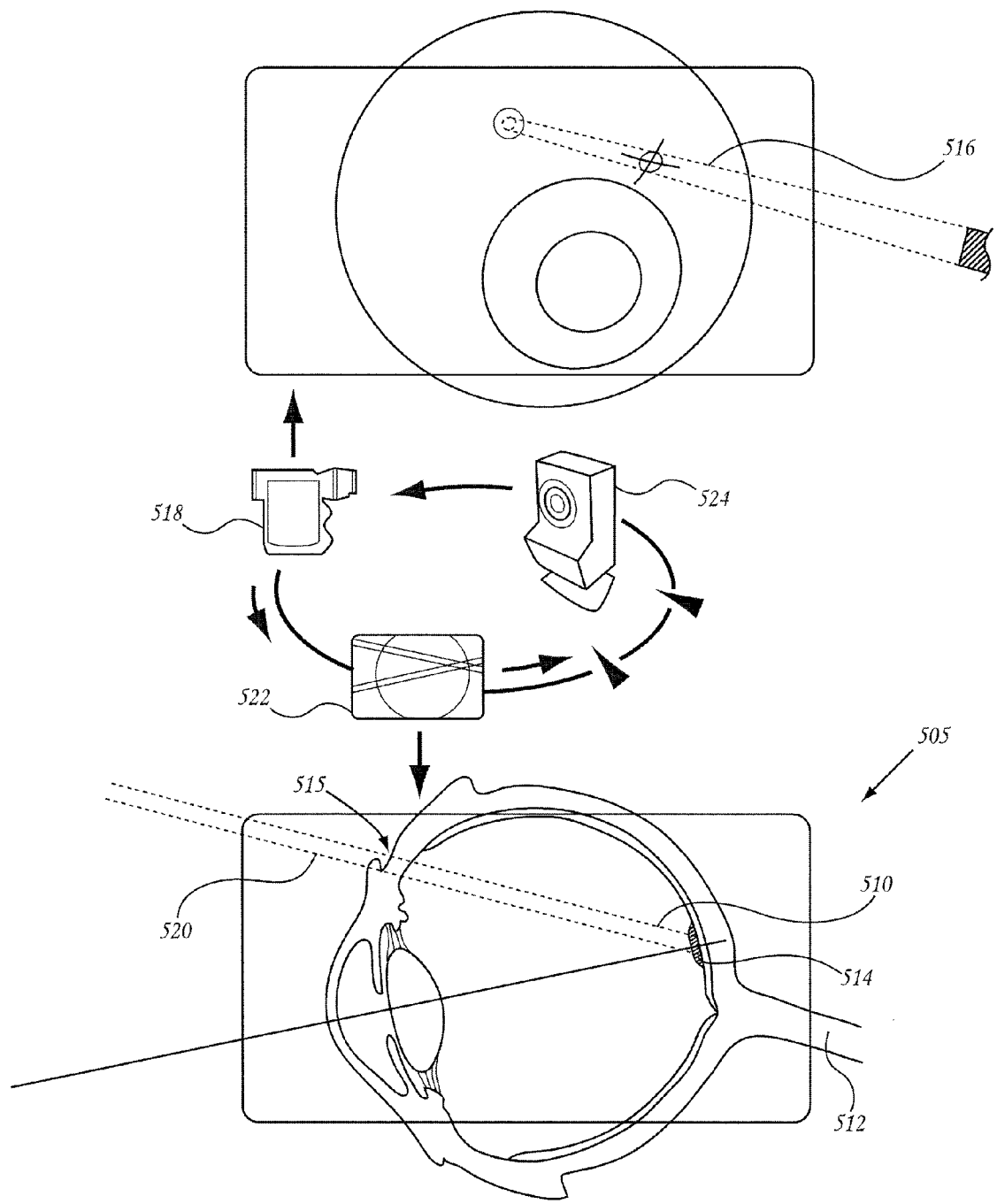
FIG. 2D illustrates some embodiments of a radiotherapy system targeting a location within an eye for treatment.

The x-ray coupling subsystem 500 integrates with the x-ray generation subsystem 700 under the umbrella of the treatment planning system 800. Also depicted in FIG. 2A and in more detail in FIG. 2C is at least one laser pointer 1060 (1410 in FIG. 2C) which can serve multiple purposes as described. In some embodiments, the laser pointers 1060 couple with the direction of the collimated x-ray beam 1090 so that the centroid of the laser beam is approximately identical to the centroid of the x-ray beam 1090 so as to have a visible marker as to where the x-ray beam is being delivered. Because x-rays are not visible, the laser pointers serve to identify the direction of the x-ray beam relative to other parts of the radiotherapy system. Where the center of the x-ray beam is pointed, the center of the laser beam is correspondingly pointed as well as shown in FIG. 2C.

Radiotherapy Coupling Subsystem

A third major subsystem of the present disclosure is the coupling subsystem or module 500. In general terms, the coupling module 500 coordinates the direction of the x-ray beam position to the position of the eye. As depicted in FIGS. 2A-2D, embodiments includes laser pointer 1060 (one or more may be desired) that follows the direction of the x-ray beam. In some embodiments, the laser pointer(s) allow for detection of the angles of incidence of the laser beam 1500 (FIG. 3) with respect to the sclera or other surface they impinge upon. The angles of incidence 1510, 1520 can be defined by two orthogonal entrance angles ($\theta$, $\phi$) on the sclera or other surface. The centroids of the one or more laser pointers 1070 coincide with the centroid of the x-ray beam as it impinges on the sclera or other surface.

As will be described in greater detail below, the laser pointer can also serve an important purpose in the imaging subsystem which is to provide a visual mark (FIG. 3) 1570 on a surface of an eye 1600 when the eye is imaged by the camera 1550 and digitized or followed in the imaging subsystem. With the visual mark 1570 on the digitized image and the angles of incidence 1510, 1520 of the laser beam 1500, computer generated projections 1700, 1730 of the x-ray (or laser) can be produced on a computer-generated (virtual) retina 1720. In some embodiments, the projections 1700, 1730 are the same, and in some embodiments, the projections can be distinct. For example, in some embodiments, the projection 1700 external to the eye may have different characteristics (e.g., trajectory, penumbra, etc.) than does the projection 1730 within the eye.

The computer-generated virtual retina 1720 (FIG. 3) is described in further detail below and is a component of a virtual ocular model and is obtained via real data from an imaging system such as, for example, an OCT, CT Scan, MRI, A or B-scan ultrasound, a combination of these, or other ophthalmic imaging devices such as a fundoscopy and/or scanning laser ophthalmoscopy. In addition to the retina, x-ray delivery to any structure within the eye can be depicted on the virtual ocular model 1725.

Figure 3:
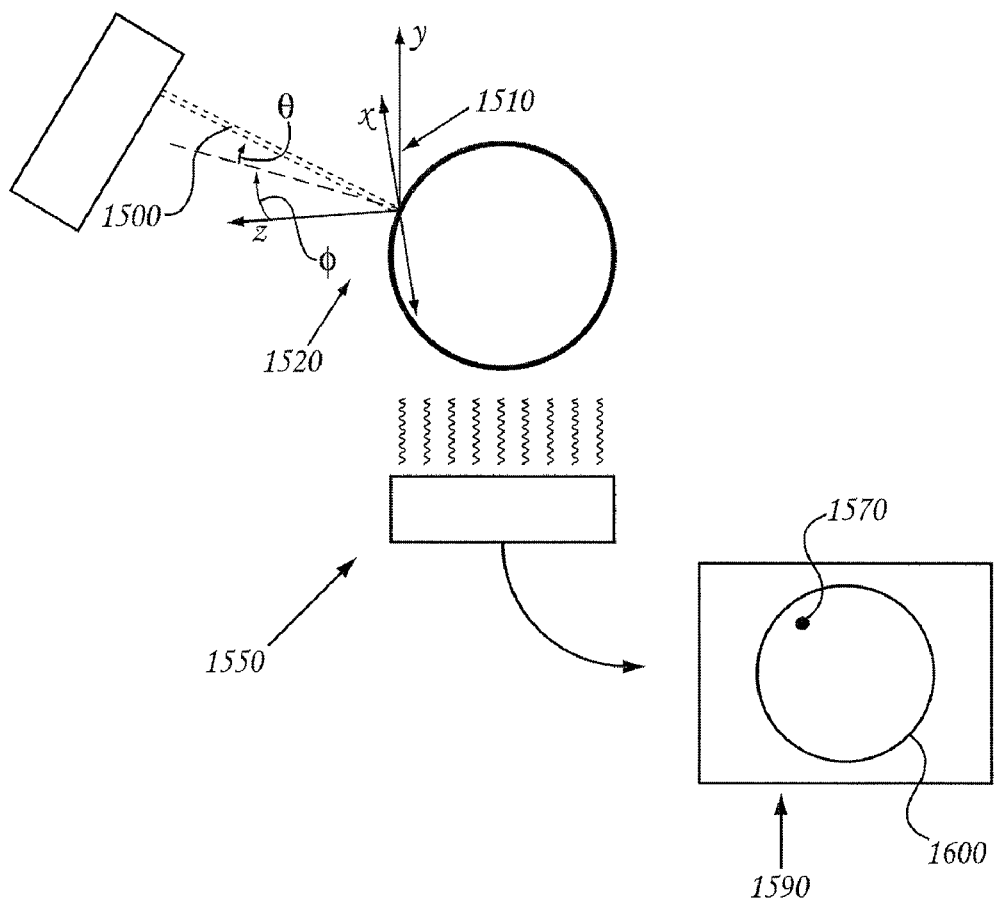
FIG. 3 depicts embodiments of a subsystem of a radiotherapy control module.
Figure 3:
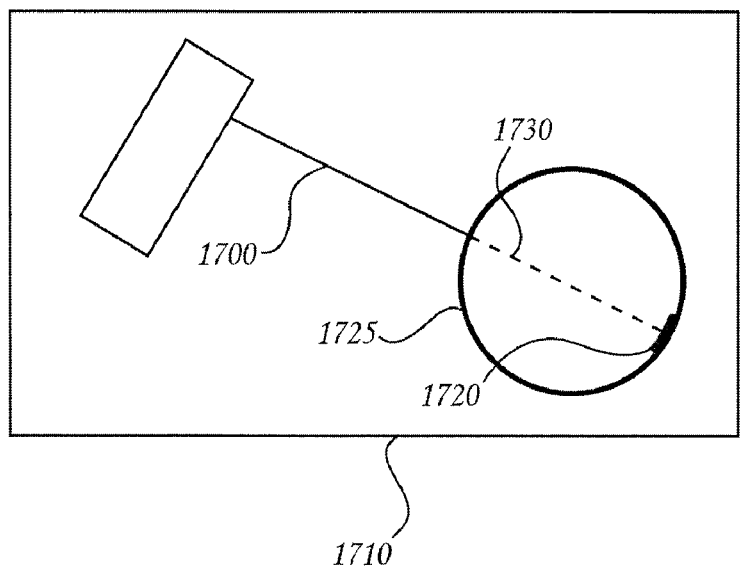

As shown in FIG. 3, laser beam 1500 is shown as the mark 1570 on screen 1590, which is a depiction of the image seen by the camera 1550 and then in digitized form within the treatment planning system 800. With angles θ 1520 and φ 1510 and the location of the mark 1570 of the laser pointer on the digitized image of the eye 1600, the path 1730 through a "virtual eye" 1725 can be determined in a computer system 1710. If the position is not correct, a signal can be sent back to the electromotive module in order to readjust the targeting point and/or position of the laser/x-ray.

In certain embodiments, a second camera can be used to so as to detect the angles of the laser pointer and x-ray beam. These angles can be used to detect the direction of the x-ray beam and send a signal to the electromotive system for re-positioning. This feedback system can ensure proper positioning of the electromotive subsystem as well as correct dosing of the x-ray irradiation to the eye.

In some embodiments, an analogue system is used to detect the position of the eye. In these embodiments, the target structure, the eye, is assumed to be in a position and the x-ray control system positions the x-ray source around the globe of the eye, then applying the pre-determined amount of radiation to the eye structure.

In certain embodiments, as depicted in FIG. 1E, a physical connection to the eye is used for direct coupling between the eye and the radiotherapy system. In these embodiments, a connection between the eye and the system can be mediated by a lens, such as a scleral or corneal contact lens 940. A physical link between the lens 940 and the system 10 is then provided by structure 175 which directly links to the radiotherapy system 10. The scleral lens 940 can be a soft or hard lens. The lens 940 can further contain one or more connections so that suction can be applied to the sclera so as to stabilize the eye during the therapy. The scleral lens 940 and associated attachments can be used to localize the eye in space. When the position of the sclera is known with the lens, the position of the eye is known as well. The eye is then coupled to the radiotherapy device 10. In some embodiments, the connection between the contact lens and the radiotherapy device 10 is a non-mechanical connection in that the connection is an optical one such as with a laser pointer or one or more cameras to detect the actual position of the eye relative to the radiotherapy system. The position of the eye in physical space is used to simulate the position of the beams in the virtual eye model and then back to the physical world to place the x-ray system to deliver the desired beam direction, angles, positions, treatment times, etc.

In some instances, it is desirable to know the scatter dose of the x-ray beam being delivered to a treated structure within the eye. For example, when neovascularization is being treated in the retina with a beam traveling through the sclera, scatter to the lens or optic nerve may be modeled. In further instances, it may be desired to know the dose to the neovascular membrane on the retina, the primary structure to be treated.

Imaging Subsystem

Figure 4:
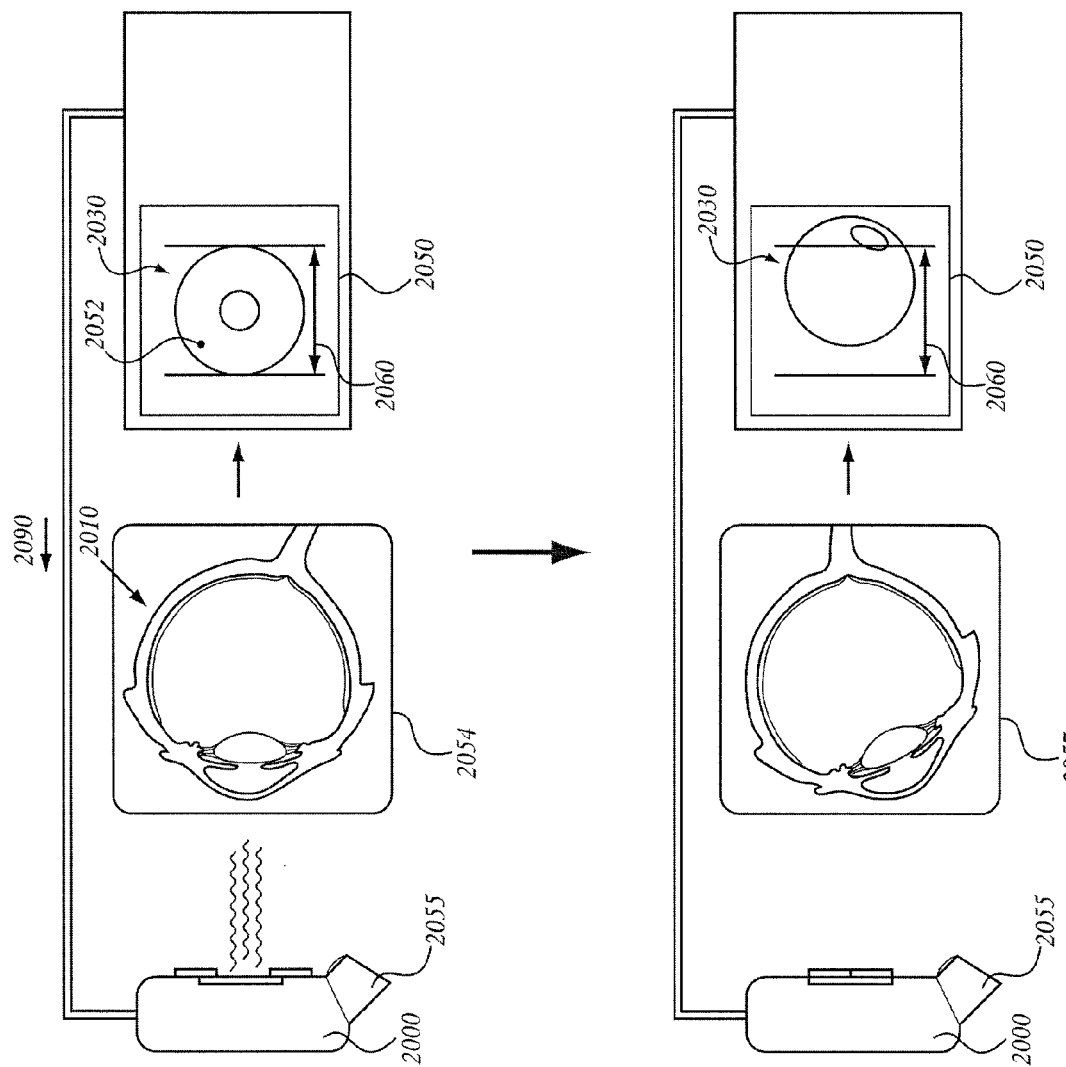
FIG. 4 illustrates a side view of an eye wherein eye location is tracked according to certain methods.

A fourth advantageous feature of the present disclosure is the imaging subsystem 400, which can also serves as an eye tracking system (FIG. 4) and offers the ability to couple patient movement or eye movement with the other subsystems above. This subsystem 400 advantageously ensures that the patient's eye 2010 does not grossly move out of the treatment field 2060. Camera 2055 can be the same camera 1550 in FIG. 3. The camera 2055 delivers an image to screen 2050. The imaged laser spot 2052 is also shown on screen 2050. The video screen 2050 can be the same video screen 1710 in FIG. 3. Field 2060 in FIG. 4 is the zone within which the eye can move; if the eye 2010 moves outside the zone 2060 on the screen, then the radiation source is either turned off, shuttered off, or otherwise disengaged from the eye 2010. In some embodiments, when an image of the eye 2030 reflects that the eye 2010 has moved out of field 2060, a signal 2090 is sent to the x-ray control system (FIG. 2A) to turn the shutter off. Aside from ensuring that the eye remains within the treatment field, the imaging system couples to the other subsystems by enabling projection of the laser pointer/x-ray beam 2052 on the back of the computer generated virtual eye.

In some embodiments, the imaging subsystem is composed of two or more cameras which are used to create a three-dimensional rendering of the eye in space, the three-dimensional rendering then integrated into the overall treatment scheme.

Treatment Planning System

The treatment planning system 800 is, in part, a virtual system and is depicted in FIG. 1A; it integrates all of the inter-related modules and provides an interface for the health care provider as well. The planning system 800 is the "brains" of the system 10 and provides the interface between the physician prescribing the therapy and the delivery of the therapy to the patient. The treatment planning system integrates anatomic, biometric, and in some cases, geometric assumptions about the eye "the virtual eye model" with information about the patient, the disease, and the system. The information is preferably incorporated into a treatment plan, which can then direct the radiation source to apply specific doses of radiation to specific regions of the eye, the doses being input to and output from the treatment planning system 800. In certain embodiments of the treatment planning system 800, treatment with radiation may be fractionated over a period of days, weeks, or months to allow for repair of tissues other than those that are pathologic or to be otherwise treated. The treatment planning system 800 can allow the physician to map the treatment and dose region and to tailor the therapy for each patient.

Figure 2E:
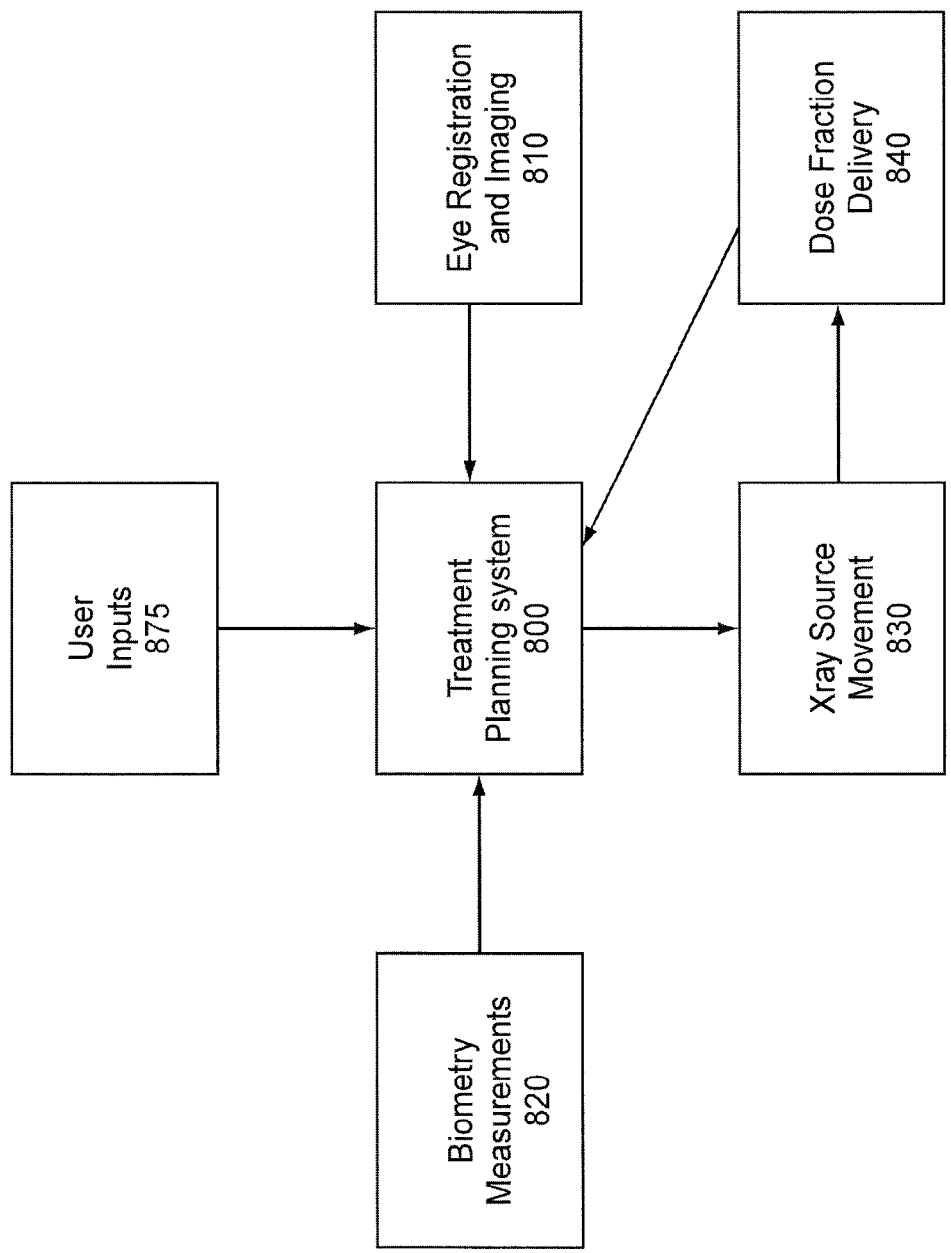
FIG. 2E illustrates a schematic view of a radiotherapy system and a method of clinical application of the system.

Referring to FIG. 2E, the treatment planning system 800 forms the center of a method of treatment using radiosurgery system 10. In certain embodiments, the imaging module 400 of the system 10 includes an eye registration and imaging system 810. In certain embodiments, the eye-tracking system is configured to track patient movement, such as eye movement, for use by the treatment planning system 800. The eye-tracking system 810 can calculate a three-dimensional image of the patient's eye via physician inputs, and can include real-time tracking of movement of the patient's eye. The eye-tracking system obtains data that becomes a factor for determining radiotherapy treatment planning for a number of medical conditions relating to the eye, as described above. For example, the eye-tracking system may create an image of the posterior region of the patient's eye using the data it obtains. In certain embodiments, the data can be transferred via cable communication or other means, such as wireless means, to the processing module 140 of the radiotherapy treatment system 10. In certain embodiments, the processing module 140 may process data on the patient's eye and present an image of the patient's eye on the interface display 130. In certain embodiments, the interface display 130 may present a real-time image of the patient's eye, including movement of the eye.

In certain embodiments, the eye-tracking system obtains data on the patient's eye while the patient's face is placed approximately upright on and secured by the articulated head restraint 160 such that the patient's eyes face substantially forward, in the direction of the imaging module 400. In certain embodiments, the eye-tracking system may include an alignment system, adjustable using a joystick. The joystick can be tilted horizontally, vertically, or both horizontally and vertically, on a fixed base, in order to adjust the location and/or image displayed on the interface display 130 by the imaging module 400.

Another feature of the present disclosure is an integrated plan for treatment. The scale of the device as well as a limitation that the device treat a specific anatomy limits the scope of the treatment planning system which also allows for economies of scale. It is preferable that the x-ray beams be focused so that they apply radiation selectively to target regions of the eye and not to other regions of the eye to which high x-ray doses could be toxic. However, in some embodiments, the eye is the only anatomic region that is treated. In certain embodiments, the retina is the target for the ophthalmic treatment system; one or more beams would be directed to regions of the retina as they pass through the sclera. For treatment planning purposes, it is preferable to know the three-dimensional position of the eye and retina with respect to the output beam of the system. The treatment planning system incorporates detailed images and recreates the geometry of the eye and subsequently directs the x-ray system to manipulate the x-ray output so that the output beam points in the target direction. In some embodiments, the x-ray system is directed and moved automatically.

The treatment planning system 800 may utilize, or be coupled to, imaging systems such as, for example, optical coherence tomography systems (OCT), ultrasound imaging systems, CT scans, MRI, PET, slit lamps microscopy systems, direct visualization, analogue or digital photographs (collectively referred to as Biometry Measurements 820). In some embodiments, these systems are integrated into real-time feedback systems with the radiotherapy device such that second be second system updates of eye position and status can take place. Although relatively sophisticated, the system 800 would be limited to the ophthalmic region and therefore takes advantage of specific imaging equipment only available for the eye.

In some embodiments, the treatment planning system incorporates the entire soft tissue and bony structures of the head of a patient. The model incorporates all the anatomic structures so that obstructing anatomic regions can be excluded from the treatment. For example, the treatment plan incorporates the nose, the forehead, and associated skin and cartilage to dictate the directionality of the radiotherapy beam with respect to the eye. In some embodiments, these structures are related to the global coordinate system and aid in tracking and treating regions of the eye.

In some embodiments, the treatment planning system incorporates physical modeling techniques such as Monte Carlo (MC) simulation into the treatment plan so that the real time x-ray doses can be delivered to the ocular structures. In these embodiments, the inputs to the treatment planning system 800 are integrated with Monte Carlo simulation of the planned treatment plan and the effects of the plan, both therapeutic and potentially toxic, can be simulated in real time.

The method depicted in FIG. 2E is as follows. Biometry measurements 820 and user controls 875 such as structure and dose are entered into the treatment planning system 800. Other inputs include information from an eye registration and imaging system 810. The output from the treatment planning system 800 consists of commands sent to the x-ray source and electromotive subsystem to move and position the source as well as to direct the on and off times (dose control) of the x-ray source 830. After a dose 840 is delivered, the treatment planning system 800 then signals x-ray source movement to deliver an additional dose 840. This cycle can iterate several times until the treatment is completed.

For example, if a single beam can deliver the desired amount of radiation, the treatment planning system determines the direction of the xray beam relative to the patient specific anatomy and then the xray source is turned on. If two beams are desired to create the dose accumulation to the target, then the treatment planning system determines the size of the beams, their angles relative to the target and the specific patient anatomy, then applies the first beam to the eye in a first angle and a second beam at a second angle relative to the target. A similar method is used for three, four, five, or six beams.

Monte Carlo Simulation and Experimental Validation

Monte Carlo (MC) simulation is the gold standard to model x-ray absorption, scatter, and dosing to structures impinged on by the x-ray. Monte Carlo methods are a widely used class of computational algorithms for simulating the behavior of various physical and mathematical systems, and for other computations. They are distinguished from other simulation methods (such as finite element modeling) by being stochastic, that is, non-deterministic in some manner. Monte Carlo simulation forms an integral part of all treatment planning systems and is used to assist in treatment planning where radiation is involved. Monte Carlo simulation can also be used to predict and dictate the feasibility and other elements of the radiotherapy system 10 (e.g., optimization of the collimator and treatment planning schemes); for example, the collimation designs, the energy levels, and the filtering regimes, can be predicted using Monte Carlo simulation. The designs predicted by Monte Carlo simulation should be experimentally verified and fine-tuned but MC simulation can predict the initial specifications.

In some embodiments, MC simulation is integrated into the treatment planning systems and in other embodiments, MC simulation dictates the algorithms used by the treatment planning system 800. MC simulation is often used in the back end of the treatment planning system to create boundaries of treatment. For example, MC simulation can predict the penumbra of an x-ray beam. The penumbra of the x-ray beam is used in the virtual world to direct the x-ray beam and set boundary limits for the x-ray beam with respect to the lens, optic nerve, etc.

In some embodiments, age-related macular degeneration (AMD) is the disease treated with the x-ray generation system. In some embodiments, the x-ray system 10 is used to treat post-surgical scarring in procedures such as laser photocoagulation and laser trabeculotomy or laser trabeculectomy. In some embodiments, the x-ray system is used to treat ocular tumors. Importantly, the x-ray treatment system allows for selective irradiation of some regions and not others. In some embodiments, radiation is fractionated over a period of days, months, or weeks to allow for repair of tissues other than those which are pathologic or to be otherwise treated.

In order to A) prove that lower energy radiation can be delivered to the retina to treat AMD in a clinically relevant time period with a device on the size scale in FIG. 1, B) from a clinically relevant distance, and C) optimize some of the parameters of the treatment system for initial design specifications for the x-ray tube, an MC simulation was performed.

Figure 5:
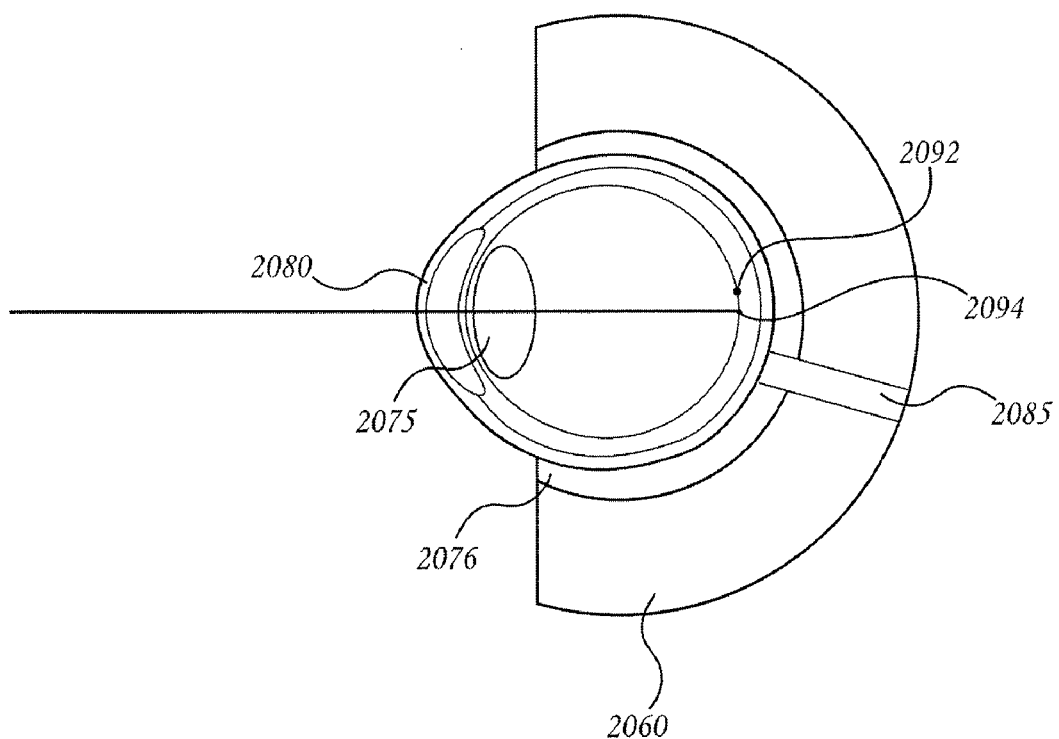
FIG. 5 illustrates a representative geometric model of the eye used for modeling purposes.
Figure 6:
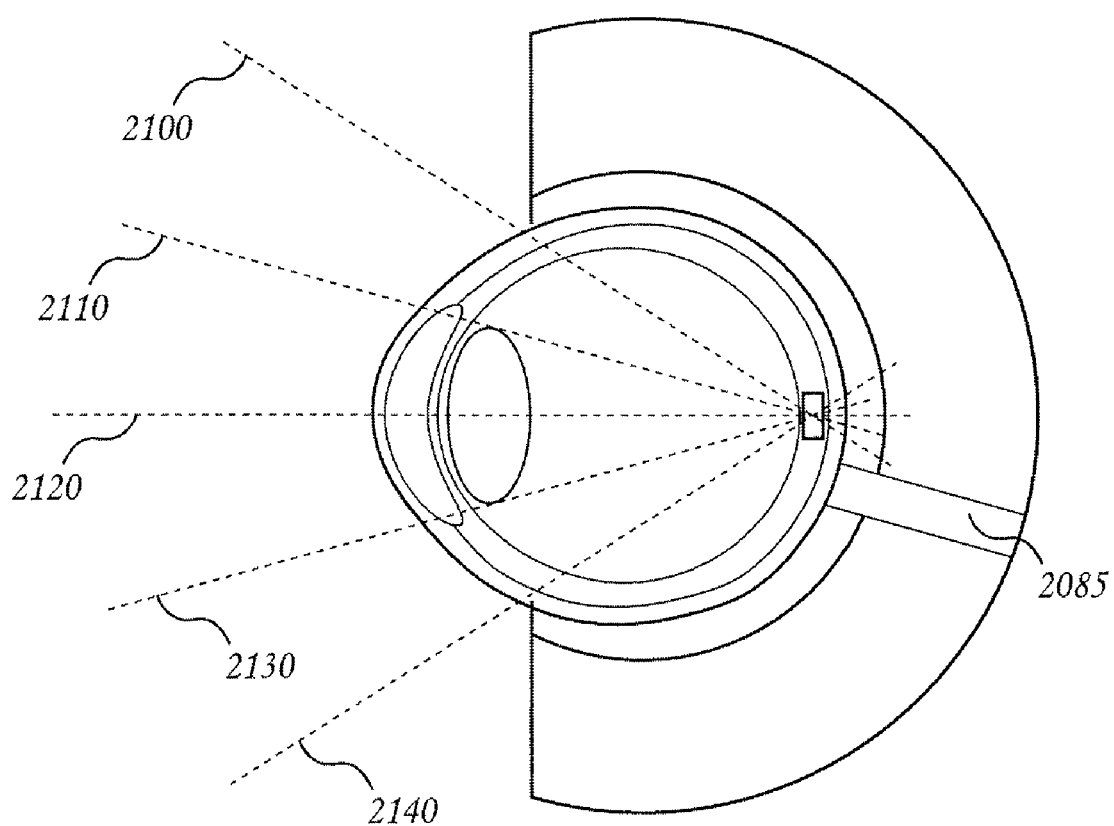
FIG. 6 illustrates representative beam angles with respect to an anterior surface and geometric axis of the eye.

Eye geometry was obtained and a two-dimensional, then three-dimensional model created, as shown in FIG. 5. Soft tissue and hard tissue (e.g., bone 2060) was incorporated into the model in FIG. 5. FIG. 6 depicts different beam angles (2100, 2110, 2120, 2130, 2140) which were modeled in this system to simulate therapy to the macula to treat AMD in this example. In this simulation, each beam enters the eye at a different angle from the geometric center 2094, or treatment axis 2096, of the eye. Each beam cuts a different path through the eye and affects different structures such as the optic nerve 2085, lens 2075, sclera 2076, cornea 2080, fovea 2092, etc. differently depending on the path through the eye. For example, beam 2120 enters the eye directly through the eye's geometric axis. A series of x-ray sources were modeled using a range of energies from 40 KeVp to 80 KeVp. A proposed collimation scheme was used to produce a near parallel beam as was a series of different filters (1-3 mm thickness aluminum). The combination of angle of entry of the beam, photon energy of the beam, and filtration of the beam all factor into the relative amounts of energy deposition to the various structures.

FIGS. 7A-7E depict some of the results from the MC simulation showing that the lower energy x-ray beams can indeed penetrate through the sclera 2200 and to the retina 2250 with minimal scatter to other ocular structures such as the lens 2260. The higher density of dots indicate actual x-ray photons in the MC simulation so that the absence of photons on the lens for example (FIG. 7A) in certain beam angles is indicative of lack of photon absorption at the level of the lens. These simulations reveal that beams with widths from about 0.5 mm to about 8.0 mm will avoid critical structures of the anterior portion of the eye at certain angles off of the central axis.

Figure 7F:
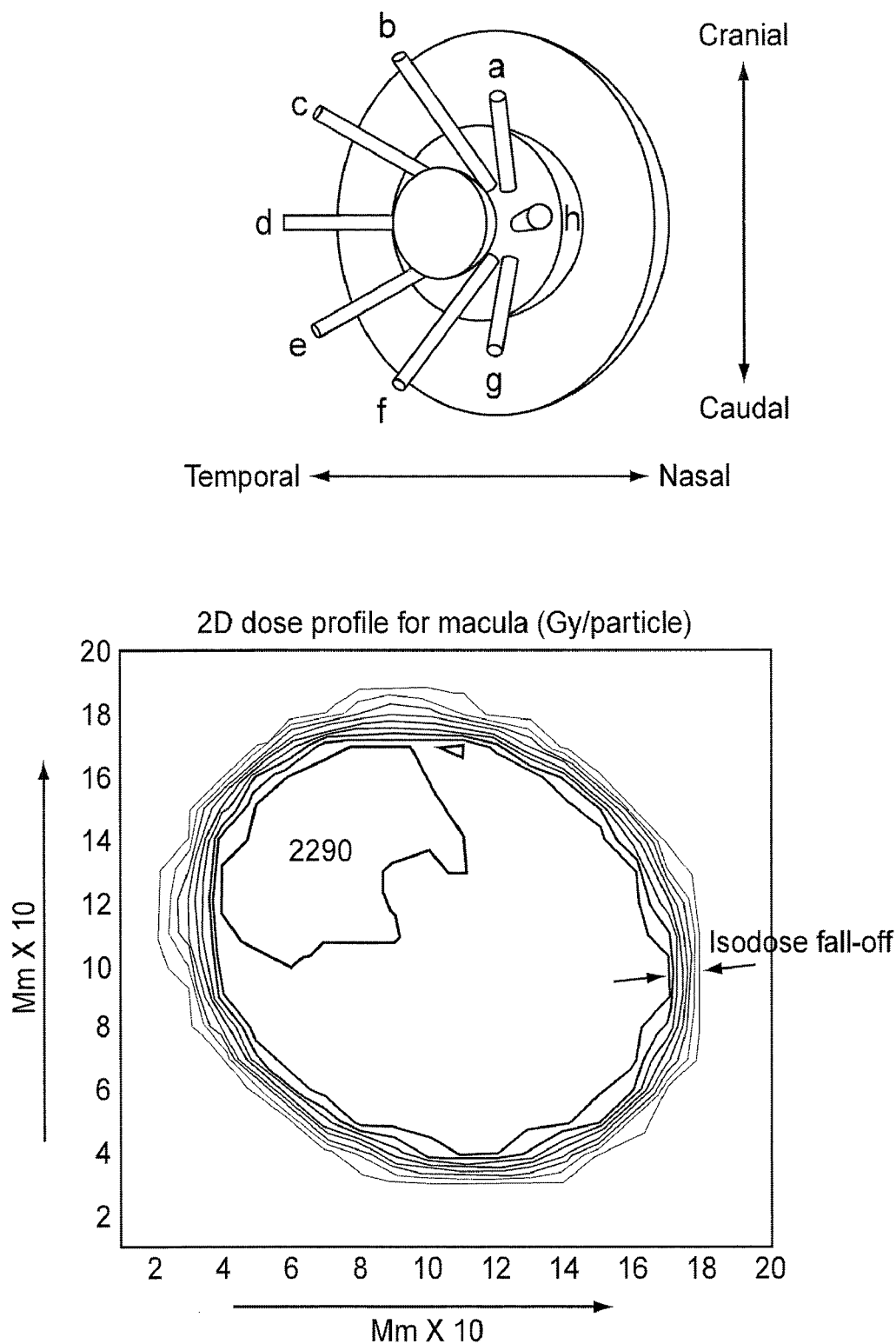

FIG. 7F depicts the results of a simulation of a series of beams which enter the eye through the pars plana region (FIGS. 7D-E). This simulation was done to minimize dose to the optic nerve with the beams in 7D and 7E which minimize dose to the structures of the front of the eye. The beam shown in 7E has the most optimum profile with respect to the optic nerve 2085 and lens 2260. Simulations with this beam are performed by directing the beam toward the eye through the pars plana direction and from various directions a-g (FIG. 7F) which correspond to varying nasal-temporal and caudal-cranial positions. In some embodiments, these beams are between 2 and 5 mm in diameter and have an energy of between 60 KeV and 150 KeV.

In some embodiments, certain angles or directions are identified as corresponding to certain structures that are desirable to avoid during treatment. Consequently, the angles that correspond to these structures are not used for the trajectory of the x-ray during treatment, thus avoiding the optic nerve. For example, in some embodiments, the angle b may correspond with an x-ray trajectory that would pass through the optic nerve. In these embodiments, the angle b may not be used to reduce the likelihood of exposing the optic nerve to the x-ray. Accordingly, the angles can be used to optimize the treatment plan and present as little risk as possible to existing structures that are sensitive to radiation. FIG. 7F depicts eight trajectory angles. In some embodiments, the x-ray trajectory can include less than eight or more than eight trajectory angles. For example, in some embodiments, four, six, ten, or twelve trajectory angles are presented. In these embodiments, optimal beam directions are provided by those beams (e.g., b, a, g, h, f) which are considered to come from the nasal direction.

The lower picture in FIG. 7F shows the dose on the retina of the angled beams in the picture above. The predicted isodose fall-off for these beams is greater than 90% within 0.05-0.1 mm of a 1-2 mm beam which is less than ten percent. Region 2290 depicts a region of higher dose within the isodose profile. This higher dose region 2290 results from the fact that the beam enters the eye at an angle. The increase in the dose is moderate at approximately ten to twenty percent higher than the average for the entire region. Furthermore, because there are multiple beams entering the eye, the areas of increased dose 2290 average out over the region of the retina. Therefore the higher dose region is incorporated into the treatment plan to account for the uneven distribution.

Figure 8:
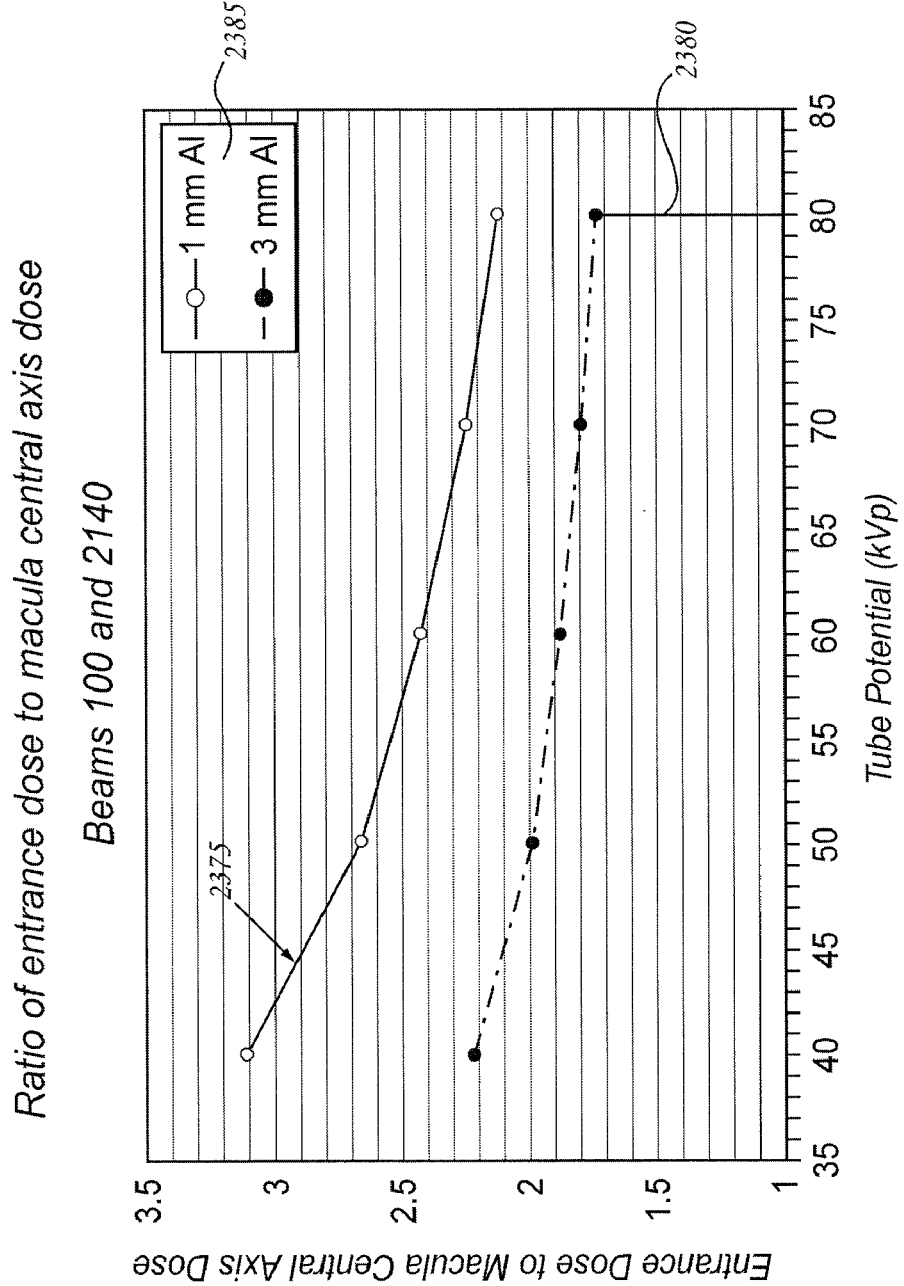
FIG. 8 depicts the results of Monte Carlo simulation performed to analyze the effect of different energies and doses on the structures of an eye.

FIG. 8 is a quantitative, graphical representation of the data in FIG. 7. What is shown is the surface to retina dose for different x-ray tube potentials and for different aluminum filter thicknesses 2385. This graph is the data for beams 2100 and 2140 in FIG. 6. The ratio of surface to retina dose is shown in FIG. 8 (i.e., the dose of entry at the sclera to the dose at the retina); what can be seen is that the dose to the sclera is not more than 3 times the dose to the retina for most beam energies (tube potentials). For energies greater than about 40 KVp, the ratio of surface dose to retina dose 2375 is less than about 3:1. What this says is that if the spot were maintained in the same position as 25 Gy was delivered to the retina, the maximum dose to the sclera would be 75 Gy. Of course, as the beam is moved around the eye, the 75 Gy is averaged over an area and becomes much less than the dose of 25 Gy to the macula. This is depicted in FIG. 6 which shows the results of the movement to different points along the sclera with the x-ray beam. At 80 KeVp 2380, the ratio of surface to depth dose is closer to 2.2 with 1 mm of filtering. These data are integrated into the treatment plan and the design of system 10 and, in part, determine the time and potential of the x-ray tube.

Therefore, in some embodiments, tightly collimated x-ray radiation at energy levels greater than 40 keV with greater than 1 mm of filtration delivered through the pars plana region of the eye can be used to deliver a therapeutic dose of radiation to the retina with a relatively lower dose buildup on the sclera, the lens, or the optic nerve than the therapeutic dose delivered to the retina. For example, if a therapeutic dose to the retina is 25 Gy or less, the dose to any region of the sclera penetrated by the beam will be less than 25 Gy.

Figure 9:
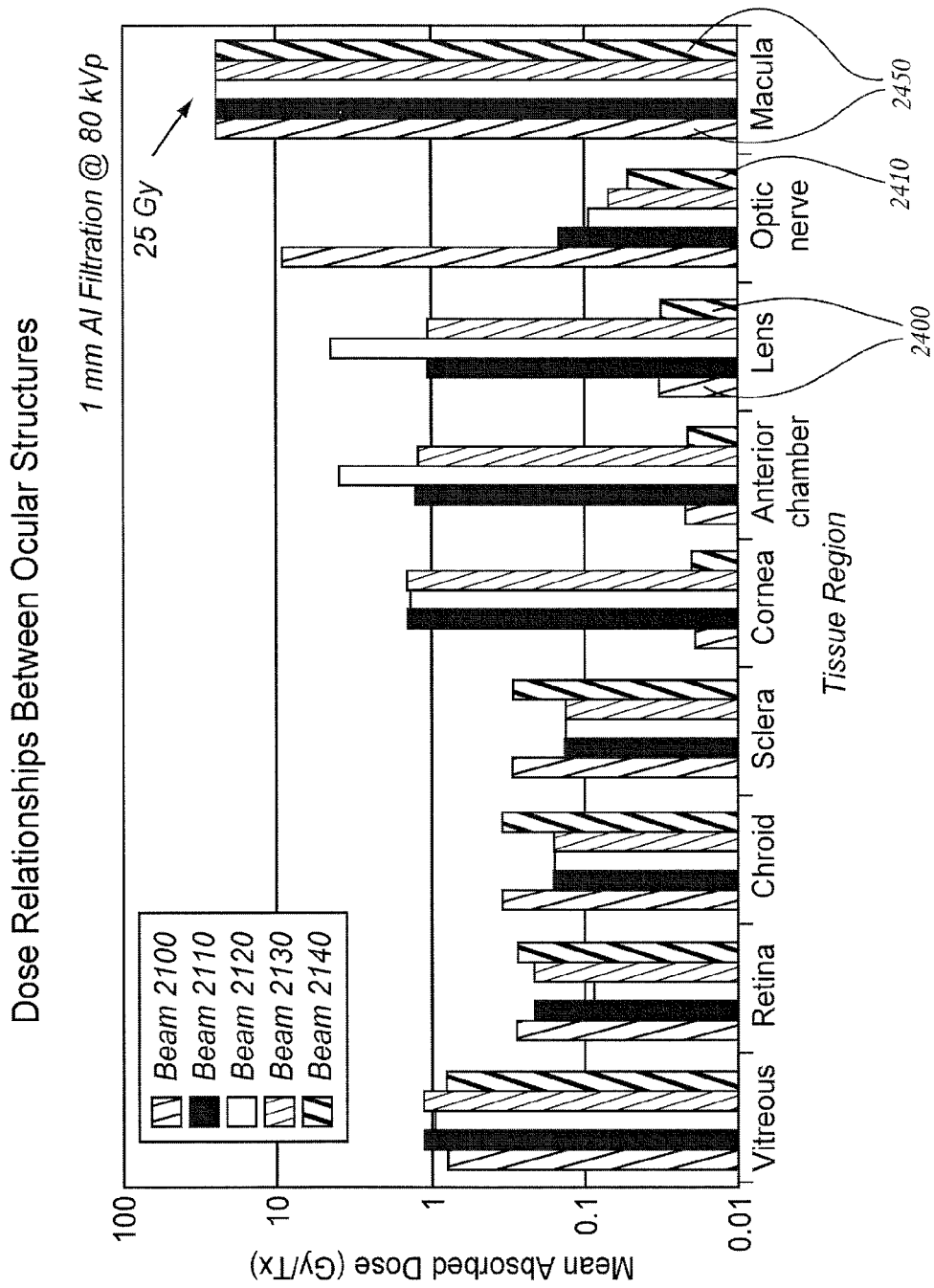
FIG. 9 depicts the results of Monte Carlo simulation performed to analyze the effect of various treatment regimes on the various structures of the eye.

FIG. 9 is a bar graph representation showing scatter doses to ophthalmic regions other than the retina and comparing them to the retina. As can be seen in the logarithmic figure, the dose to the lens 2400 (beams 2100 and 2140) and optic nerve 2410 (beam 2140 alone), the two most sensitive structures in the eye, are at least an order of magnitude lower than the dose delivered to the macular region 2450 of the retina. Therefore, a 25 Gy dose of radiation can be delivered to a region of the retina through the pars plana region of the eye with at least an order of magnitude less radiation reaching other structures of the eye such as the lens, the sclera, the choroids, etc. These simulations dictate the design specifications for the x-ray generation systems and subsystems. These simulations can also be integrated into the treatment planning system 800 as a component of the plan. For example, the planning system, which incorporates the unique anatomy of each patient, can simulate the amount of radiation delivered to each structure dependent on the angle and position of delivery through the sclera. Depending on the angle, beam size, and beam energy, the radiation delivered to the ocular structures will vary and alternative direction can be chosen if the x-ray dose is too high to the structures such as the lens and the optic nerve.

Figure 10:
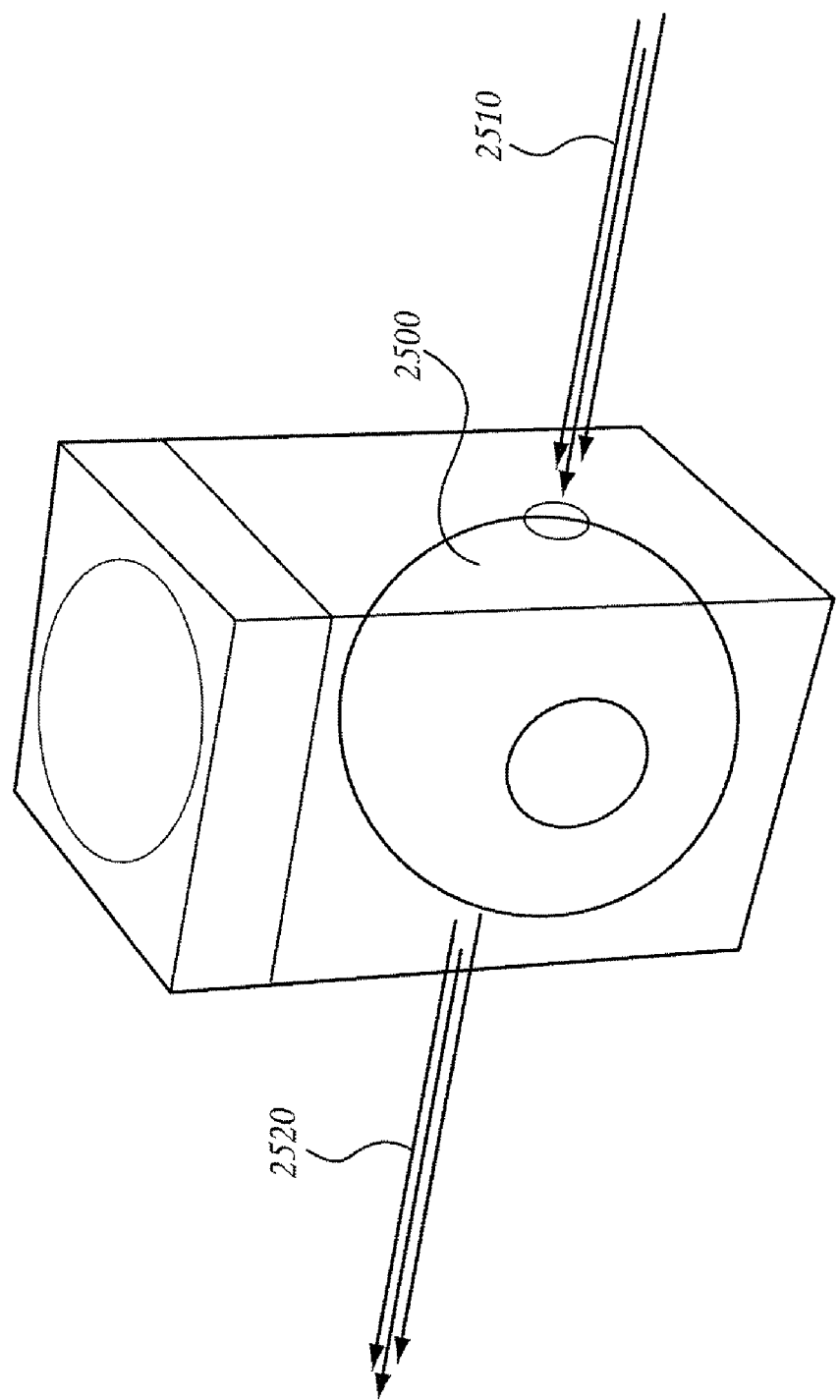
FIG. 10 depicts experimental results of thin x-ray beams traveling through a human eye to validate a Monte Carlo simulation model.

To verify the validity of the MC simulations and verify that the eye can be assumed to be a sphere of water, a human cadaver eye 2500 was obtained and the ratio of surface to depth dose of an x-ray source was experimentally determined. Among other things, parameters of an emitted x-ray beam 2510 were compared with parameters of the beam 2520 emerging from the eye 2500. The ratio from the experimental set-up in FIG. 10 proved to be identical to that when the eye is assumed to be water in the MC simulations. For example, the ratio of surface to 2 cm depth for 80 KeV with 2 mm filtration was indeed 3:1 as predicted by the MC model. Additional work verified that the dose fall off at each depth was likewise identical. This experimental work confirms that the modeling predictions using MC are accurate for ocular structures and that secondary interactions typically required of MC simulations with high energy x-rays are not necessary for lower energy x-rays. These observations significantly simplify the MC simulations and allow for quick real time simulations at the time of treatment planning. Furthermore, the design criteria which are used in the system 10 design can be accurately modeled using water for their prediction.

Further analysis and experimentation reveals that to deliver 25 Gy to the macula in a clinically relevant time period (e.g., not longer than 30 minutes), the system in FIG. 1 will draw about 1 mA to about 40 mA of current through the x-ray source. The exact number of mA depends on how close the x-ray tube is to the eye. If the tube is very close to the eye, then the system will draw less current than if the system is further away from the eye. In some embodiments, it may be that the about 15 Gy to about 25 Gy needs to be delivered to the retina in a period shorter than 10 minutes. In such an embodiment, the tube current may need to be upwards of 25 mA and the x-ray tube closer than 25 cm from the retina. These parameters are for energies of 60-100 KeV and 1-3 mm filtration with aluminum, lead, tungsten, or another x-ray absorbing metal. In certain embodiments, the collimator is less than about 5 cm from the anterior surface of the eye and the photon energy is about 100 KeV with 1, 2, 3, 4, or 5 beams with diameters of between 1 mm and 6 mm entering the eye through the infero-nasal region. The nasal region affords the greatest distance from the optic nerve and the inferior region is preferred so as to avoid the bones of the nose and the anterior skull. These assumption are for an eye which is positioned to look straight outward from the skull. In this embodiment, the treatment time may be less than about 5 minutes within a range of currents between 15 mA and 40 mA. Each beam of the 1-4 beams can be turned on for between 3 seconds and 5 minutes. In some embodiments, 3 beams are used for the treatment. In some embodiments, the collimator is placed within 3 cm from the surface of the eye, and in some embodiments, the collimator is placed within 10 cm of the surface of the eye.

Figure 11B:
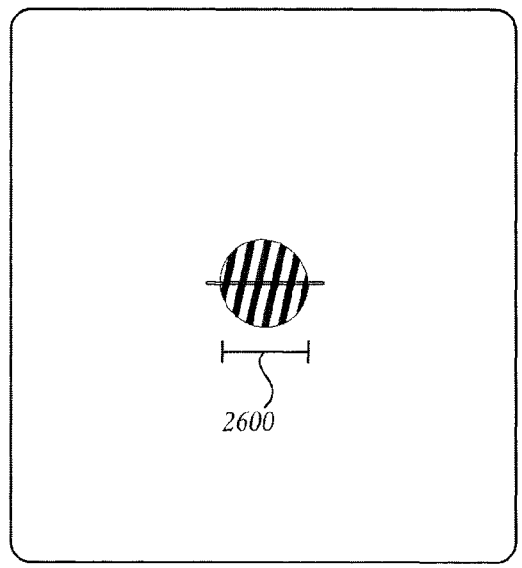
FIGS. 11A$^1$-11B depict the results of thin x-ray beams penetrating through an ophthalmic phantom to investigate penumbra and dosage variables.
Figure 11B:
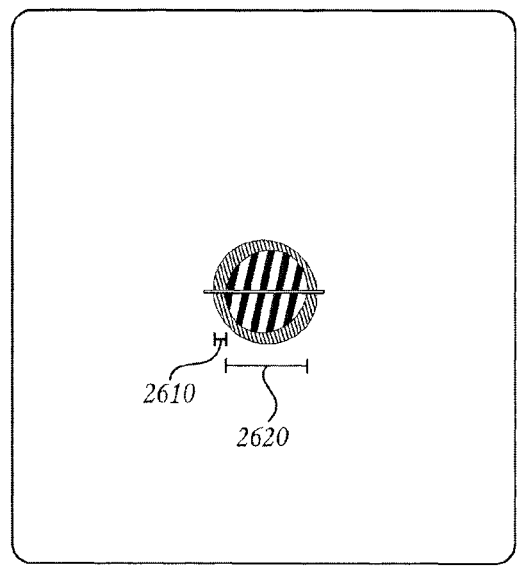
Figure 11B:
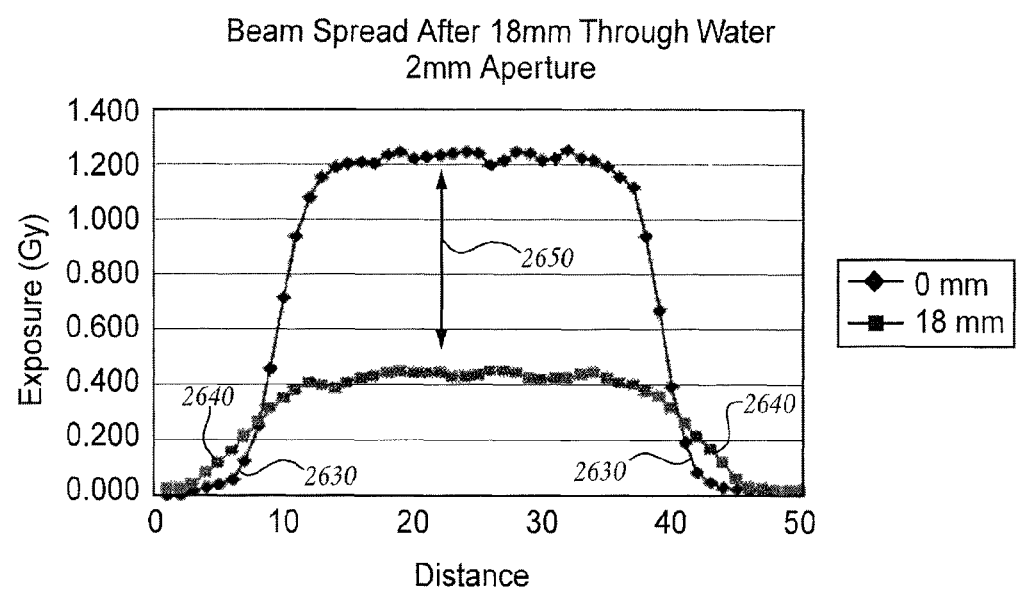

FIG. 11A depicts the results of a collimated x-ray beam 2600 which penetrates approximately 2 cm through water (or an eye) 2630 where the collimator is approximately 5.0 cm from the surface of the water. As can be seen in FIG. 11A², there is a small penumbra width 2610 about an original beam width 2620 after penetration through the eye which is less than 10% of the shaping beam shown in FIG. 11A¹. These data incorporate both divergence as well as isodose drop off and reveal that for a collimator within about 5 cm of the target, the penumbra can be very small. FIG. 11B depicts a graphical representation of the penumbra from measurements within a film. Delta 2650 represents the absorption in the energy between the surface and the depth as recorded by x-ray sensitive film. The tails seen in 2640 versus 2630 indicate a small degree of penumbra effect as the beam loses energy through the eye. Indeed, the penumbra for a 0.5 mm to 6 mm spot size can be as low as 0.01% and as high as ten percent depending on the placement of the collimators with respect to the eye.

Combination Therapy

Radiotherapy device 10 can be used in combination with other therapeutics for the eye. Radiotherapy can be used to limit the side effects of other treatments or can work synergistically with other therapies. For example, radiotherapy can be applied to laser burns on the retina or to implants or surgery on the anterior region of the eye. Radiotherapy can be combined with one or more pharmaceutical, medical treatments, and/or photodynamic treatments or agents. As used herein, "photodynamic agents" are intended to have their plain and ordinary meaning, which includes, without limitation, agents that react to light and agents that sensitize a tissue to the effects of light. For example, radiotherapy can be used in conjunction with anti-VEFG treatment, VEGF receptors, steroids, anti-inflammatory compounds, DNA binding molecules, oxygen radical forming therapies, oxygen carrying molecules, porphyryn molecules/therapies, gadolinium, particulate based formulations, oncologic chemotherapies, heat therapies, ultrasound therapies, and laser therapies.

In some embodiments, radiosensitizers and/or radioprotectors can be combined with treatment to decrease or increase the effects of radiotherapy, as discussed in Thomas, et al., Radiation Modifiers: Treatment Overview and Future Investigations, Hematol. Oncol. Clin. N. Am. 20 (2006) 119-139; Senan, et al., Design of Clinical Trials of Radiation Combined with Antiangiogenic Therapy, Oncologist 12 (2007) 465-477; the entirety of both these articles are hereby incorporated herein by reference. Some embodiments include radiotherapy with the following radiosensitizers and/or treatments: 5-fluorouracil, fluorinated pyrimidine antimetabolite, anti-S phase cytotoxin, 5-fluorouridine triphosphate, 2-deoxyfluorouridine monophosphate (Fd-UMP), and 2-deoxyfluorouridine triphosphate capecitabine, platinum analogues such as cisplatin and carboplatin, fluoropyrimidine, gemcitabine, antimetabolites, taxanes, docetaxel, topoisomerase I inhibitors, Irinotecan, cyclo-oxygenase-2 inhibitors, hypoxic cell radiosensitizers, antiangiogenic therapy, bevacizumab, recombinant monoclonal antibody, ras mediation and epidermal growth factor receptor, tumor necrosis factor vector, adenoviral vector Egr-TNF (Ad5.Egr-TNF), and hyperthermia. In some embodiments, embodiments include radiotherapy with the following radioprotectors and/or treatments: amifostine, sucralfate, cytoprotective thiol, vitamins and antioxidants, vitamin C, tocopherol-monoglucoside, pentoxifylline, alpha-tocopherol, beta-carotene, and pilocarpine.

Antiangiogenic Agents (AAs) aim to inhibit growth of new blood vessels. Bevacizumab is a humanized monoclonal antibody that acts by binding and neutralizing VEGF, which is a ligand with a central role in signaling pathways controlling blood vessel development. Findings suggest that anti-VEGF therapy has a direct antivascular effect in human tissues. In contrast, small molecule tyrosine kinase inhibitors (TKIs) prevent activation of VEGFRs, thus inhibiting downstream signaling pathways rather than binding to VEGF directly. Vascular damaging agents (VDAs) cause a rapid shutdown of established vasculature, leading to secondary tissue death. The microtubule-destabilizing agents, including combretastatins and ZD6126, and drugs related to 5,6-dimethylxanthenone-4-acetic acid (DMXAA) are two main groups of VDAs. Mixed inhibitors, including agents such as EGFR inhibitors or neutralizing agents and cytotoxic anticancer agents can also be used.

Radiodynamic Therapy

Radiodynamic therapy refers to the combination of collimated x-rays with a concomitantly administered systemic therapy. As used herein, the term "radiodynamic agents" is intended to have its ordinary and plain meaning, which includes, without limitation, agents that respond to radiation, such as x-rays, and agents that sensitize a tissue to the effects of radiation. Similar to photodynamic therapy, a compound is administered either systemically or into the vitreous; the region in the eye to be treated is then directly targeted with radiotherapy using the eye model described above. The targeted region can be precisely localized using the eye model and then radiation can be precisely applied to that region using the PORT system and virtual imaging system based on ocular data. Beam sizes of 1 mm or less can be used in radiodynamic therapy to treat ocular disorders if the target is drusen for example. In other examples, the beam size is less than about 6 mm.

While certain aspects and embodiments of the disclosure have been described, these have been presented by way of example only, and are not intended to limit the scope of the disclosure. Indeed, the novel methods and systems described herein may be embodied in a variety of other forms without departing from the spirit thereof. The accompanying claims and their equivalents are intended to cover such forms or modifications as would fall within the scope and spirit of the disclosure.

What is claimed is:

1. A method, of applying radiation to a patient's eye, comprising:
    obtaining imaging data of at least a portion of the eye;
    identifying, based on the imaging data, a location of the macula of the eye;
    identifying a first location of a fiducial marker located in or on the eye;
    mapping a location of the macula, relative to the first location of the fiducial marker, in a coordinate system, thereby producing a mapped macula location in the coordinate system;
    positioning, based on the mapped macula location, a radiation source that applies radiation to the macula;
    emitting the radiation from the positioned radiation source to the macula; and
    positioning a contact lens, that contacts the sclera of the eye and that comprises the fiducial marker, on the eye.

2. A method, of applying radiation to a patient's eye, comprising:
    obtaining imaging data of at least a portion of the eye;
    identifying, based on the imaging data, a location of the macula of the eye;
    identifying a first location of a fiducial marker located in or on the eye;
    mapping a location of the macula, relative to the first location of the fiducial marker, in a coordinate system, thereby producing a mapped macula location in the coordinate system;
    positioning, based on the mapped macula location, a radiation source that applies radiation to the macula;
    emitting the radiation from the positioned radiation source to the macula; and
    positioning a contact lens, that contacts the cornea of the eye and that comprises the fiducial marker, on the eye.

3. The method of claim 1, further comprising collimating the emitted radiation to a radiation beam having a cross-sectional width of less than about 6 mm.

4. The method of claim 1, further comprising repositioning the radiation source based on a movement of the fiducial marker to a second location of the fiducial marker.

5. The method of claim 1, further comprising, after mapping the location of the macula, detecting a movement of the eye.

6. The method of claim 5, further comprising determining a relative relationship between a new location of the macula and the mapped macula location in the coordinate system after the detecting of the eye movement.

7. The method of claim 1, further comprising emitting the radiation toward a region of drusen in the eye.

8. The method of claim 1, wherein the emitting the radiation comprises emitting an x-ray beam.

9. The method of claim 8, further comprising applying at least one additional radiation beam to the macula.

10. The method of claim 9, wherein the x-ray beam and the at least one additional radiation beam are applied simultaneously.

11. The method of claim 1, wherein the imaging data is obtained with at least one of computed tomography, magnetic resonance imaging, optical coherence tomography, and positron emission tomography.

12. The method of claim 2, further comprising collimating the emitted radiation to a radiation beam having a cross-sectional width of less than about 6 mm.

13. The method of claim 2, further comprising repositioning the radiation source based on a movement of the fiducial marker to a second location of the fiducial marker.

14. The method of claim 13, further comprising, after the repositioning of the radiation source, emitting an additional radiation beam from the radiation source to the macula.

15. The method of claim 13, further comprising, after the repositioning of the radiation source, emitting an additional radiation beam from the radiation source to the macula.

16. The method of claim 2, further comprising, after mapping the location of the macula, detecting a movement of the eye.

17. The method of claim 16, further comprising determining a relative relationship between a new location of the macula and the mapped macula location in the coordinate system after the detecting of the eye movement.

18. The method of claim 2, further comprising emitting the radiation toward a region of drusen in the eye.

19. The method of claim 2, wherein the emitting the radiation comprises emitting an x-ray beam.

20. The method of claim 19, further comprising applying at least one additional radiation beam to the macula.

21. The method of claim 20, wherein the x-ray beam and the at least one additional radiation beam are applied simultaneously.

22. The method of claim 2, wherein the imaging data is obtained with at least one of computed tomography, magnetic resonance imaging, optical coherence tomography, and positron emission tomography.

* * * * *